(12) United States Patent
Escudero et al.

(10) Patent No.: US 11,786,269 B2
(45) Date of Patent: *Oct. 17, 2023

(54) ATHERECTOMY DEVICES AND METHODS

(71) Applicant: AtheroMed, Inc., Menlo Park, CA (US)

(72) Inventors: Paul Quentin Escudero, Redwood City, CA (US); John T. To, Newark, CA (US); Christopher James Danek, San Carlos, CA (US)

(73) Assignee: ATHEROMED, INC., Menlo Park, CA (US)

( * ) Notice: Subject to any disclaimer, the term of this patent is extended or adjusted under 35 U.S.C. 154(b) by 478 days.

This patent is subject to a terminal disclaimer.

(21) Appl. No.: 15/093,942

(22) Filed: Apr. 8, 2016

(65) Prior Publication Data
US 2016/0228146 A1 Aug. 11, 2016

Related U.S. Application Data

(60) Continuation of application No. 14/751,677, filed on Jun. 26, 2015, now Pat. No. 9,333,007, which is a continuation of application No. 14/106,651, filed on Dec. 13, 2013, now Pat. No. 9,095,371, which is a continuation of application No. 13/691,485, filed on Nov. 30, 2012, now Pat. No. 8,647,355, which is a continuation of application No. 13/309,986, filed on Dec. 2, 2011, now Pat. No. 8,337,516, which is a (Continued)

(51) Int. Cl.
*A61B 17/3207* (2006.01)
*A61M 25/09* (2006.01)
*A61B 17/22* (2006.01)
*A61B 17/00* (2006.01)
*A61B 17/32* (2006.01)

(52) U.S. Cl.
CPC .. *A61B 17/320783* (2013.01); *A61B 17/3207* (2013.01); *A61B 17/320758* (2013.01); *A61M 25/09* (2013.01); *A61B 2017/00685* (2013.01); *A61B 2017/22038* (2013.01); *A61B 2017/22047* (2013.01); *A61B 2017/22048* (2013.01); *A61B 2017/22068* (2013.01); *A61B 2017/22082* (2013.01); *A61B 2017/320064* (2013.01)

(58) Field of Classification Search
CPC .. A61B 17/320758; A61B 2017/22047; A61B 2017/22048; A61B 2017/22068; A61B 2017/22038; A61B 2017/22082
See application file for complete search history.

(56) References Cited

U.S. PATENT DOCUMENTS

| | | | | |
|---|---|---|---|---|
| 3,945,375 A | * | 3/1976 | Banko | A61B 10/04 600/104 |
| 4,745,919 A | * | 5/1988 | Bundy | A61B 17/3207 600/564 |

(Continued)

FOREIGN PATENT DOCUMENTS

WO    WO-0054659 A1 * 9/2000 ..... A61B 17/320758

*Primary Examiner* — Diane D Yabut
*Assistant Examiner* — Rachel S Highland

(57) ABSTRACT

The devices and methods generally relate to treatment of occluded body lumens. In particular, the present devices and method relate to removal of the occluding material from the blood vessels as well as other body lumens.

17 Claims, 33 Drawing Sheets

Related U.S. Application Data division of application No. 12/288,593, filed on Oct. 22, 2008, now Pat. No. 8,070,762.

(60) Provisional application No. 60/981,735, filed on Oct. 22, 2007.

(56) References Cited

U.S. PATENT DOCUMENTS

| | | | | |
|---|---|---|---|---|
| 5,417,703 | A | * | 5/1995 | Brown .................. A61B 17/22 606/159 |
| 5,876,414 | A | * | 3/1999 | Straub ............ A61B 17/320783 604/22 |
| 7,235,088 | B2 | * | 6/2007 | Pintor ............ A61B 17/320758 606/159 |
| 2002/0007190 | A1 | * | 1/2002 | Wulfman ....... A61B 17/320758 606/171 |
| 2008/0004643 | A1 | * | 1/2008 | To .................. A61B 17/320783 606/159 |
| 2008/0004645 | A1 | * | 1/2008 | To .................. A61B 17/320783 606/159 |
| 2009/0024085 | A1 | | 1/2009 | To et al. |
| 2009/0234378 | A1 | | 9/2009 | Escudero |
| 2010/0010492 | A1 | | 1/2010 | Lockard et al. |
| 2010/0049225 | A1 | | 2/2010 | To et al. |
| 2010/0174302 | A1 | | 7/2010 | Heitzmann et al. |
| 2010/0324567 | A1 | | 12/2010 | Root et al. |
| 2010/0324576 | A1 | | 12/2010 | Pintor et al. |
| 2011/0040315 | A1 | | 2/2011 | To et al. |
| 2011/0112563 | A1 | | 5/2011 | To et al. |
| 2011/0152906 | A1 | | 6/2011 | Escudero et al. |
| 2011/0152907 | A1 | | 6/2011 | Escudero et al. |
| 2011/0270289 | A1 | | 11/2011 | To et al. |
| 2011/0301626 | A1 | | 12/2011 | To et al. |
| 2012/0083810 | A1 | | 4/2012 | Escudero et al. |
| 2013/0085515 | A1 | | 4/2013 | To et al. |
| 2013/0090674 | A1 | | 4/2013 | Escudero et al. |
| 2013/0096587 | A1 | | 4/2013 | Smith et al. |
| 2013/0103062 | A1 | | 4/2013 | To et al. |
| 2013/0103063 | A1 | | 4/2013 | Escudero et al. |
| 2013/0158578 | A1 | | 6/2013 | Ghonke et al. |
| 2013/0296901 | A1 | | 11/2013 | Olson |
| 2014/0039532 | A1 | | 2/2014 | Vrba |
| 2014/0058423 | A1 | | 2/2014 | Smith et al. |
| 2014/0107680 | A1 | | 4/2014 | Escudero et al. |

* cited by examiner

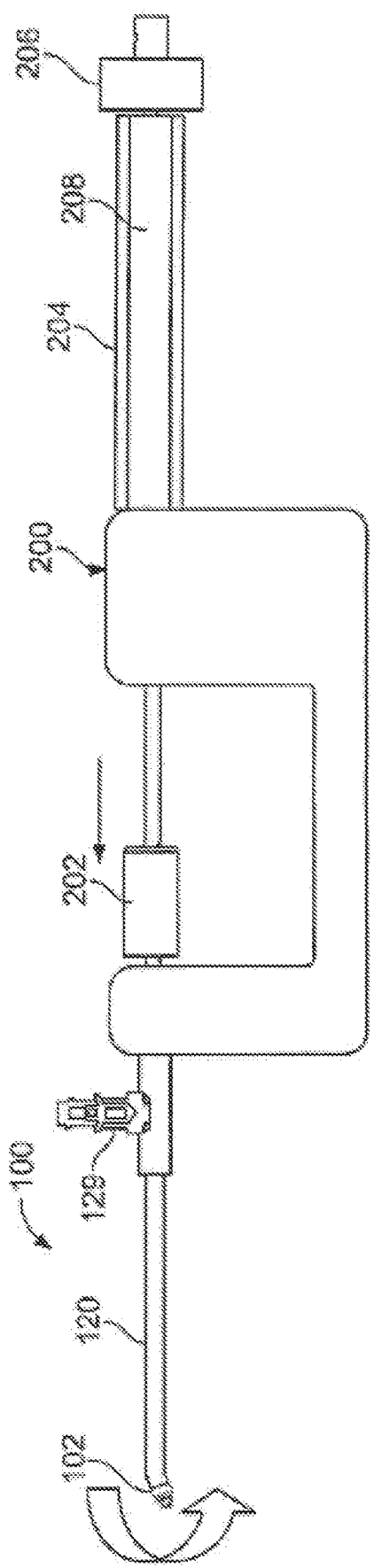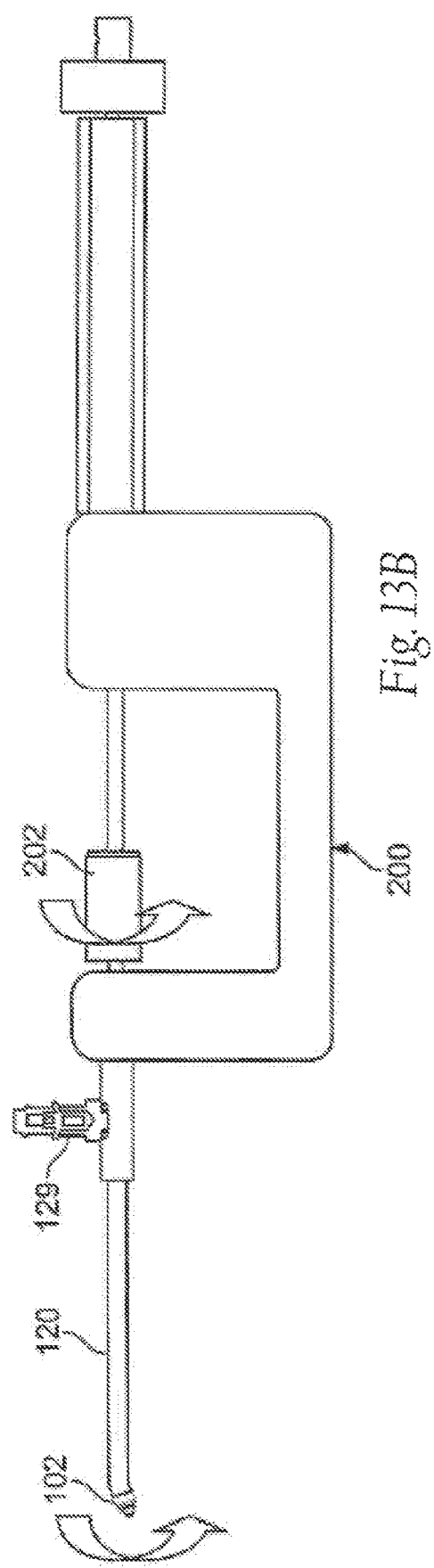

ATHERECTOMY DEVICES AND METHODS

RELATED APPLICATIONS

This application is a continuation of U.S. patent application Ser. No. 14/751,677, filed Jun. 26, 2015, which is a continuation of U.S. patent application Ser. No. 14/106,651 (now U.S. Pat. No. 9,095,371), filed Dec. 13, 2013, which is a continuation of U.S. patent application Ser. No. 13/691,485 (now U.S. Pat. No. 8,647,355), filed Nov. 30, 2012, which is a continuation of U.S. patent application Ser. No. 13/309,986 (now U.S. Pat. No. 8,337,516), filed Dec. 2, 2011, which is a divisional of U.S. patent application Ser. No. 12/288,593 (now U.S. Pat. No. 8,070,762), filed Oct. 22, 2008, entitled "Atherectomy Devices and Methods," which claims the benefit of and priority to U.S. Provisional Patent Application Ser. No. 60/981,735, filed Oct. 22, 2007, and entitled "Atherectomy Devices and Methods," the disclosure of each of which is incorporated herein by reference in its entirety.

FIELD OF THE INVENTION

The devices and methods described below generally relate to treatment of occluded body lumens. In particular, the present devices and method relate to improved devices for removal of the occluding material from the blood vessels as well as other body lumens.

BACKGROUND OF THE INVENTION

Atherosclerosis is a progressive disease. In this disease, lesions of the arteries are formed by accumulation of plaque and neointimal hyperplasia causing an obstruction of blood flow. Often plaque is friable and may dislodge naturally or during an endovascular procedure, leading to embolization of a downstream vessel.

Endovascular clearing procedures to reduce or remove the obstructions to restore luminal diameter allows for increased blood flow to normal levels are well known. Removing the plaque has the effect of removing diseased tissue and helps to reverse the disease. Maintaining luminal diameter for a period of time (several to many weeks) allows remodeling of the vessel from the previous pathological state to a more normal state. Finally, it is the goal of an endovascular therapy to prevent short term complications such as embolization or perforation of the vessel and long term complications such as ischemia from thrombosis or restenosis.

Various treatment modalities may help to accomplish treatment goals. In atherectomy, plaque is cut away, or excised. Various configurations are used including a rotating cylindrical shaver or a fluted cutter. The devices may include shielding by a housing for safety. The devices may also remove debris via trapping the debris in the catheter, in a downstream filter, or aspirating the debris. In some cases a burr may be used instead of a cutter, particularly to grind heavily calcified lesions into very small particle sizes. Aspiration may also be used with a burr-type atherectomy device.

Balloon angioplasty is another type of endovascular procedure. Balloon angioplasty expands and opens the artery by both displacing the plaque and compressing it. Balloon angioplasty is known to cause barotrauma to the vessel from the high pressures required to compress the plaque. This trauma leads to an unacceptably high rate of restenosis. Furthermore, this procedure may not be efficient for treatment of elastic-type plaque tissue, where such tissue can spring back to occlude the lumen.

When clearing such obstructions it is desirable to protect the vessel well or wall of the body lumen being cleared and to debulk substantially all of a lesion. In additional cases, the procedure that clears obstructions may also be coupled with placement of an implant within the lumen. For example, it may be desirable to deploy a stent to maintain patency of a vessel for a period of time and/or to achieve local drug delivery by having the stent elute a drug or other bioactive substance.

On their own, stents fail to perform well in the peripheral vasculature for a variety of reasons. A stent with the necessary structural integrity to supply sufficient radial force to reopen the artery often does not perform well in the harsh mechanical environment of the peripheral vasculature. For example, the peripheral vasculature encounters a significant amount of compression, torsion, extension, and bending. Such an environment may lead to stent failure (strut cracking, stent crushing, etc.) that eventually compromises the ability of the stent to maintain lumen diameter over the long-term. On the other hand, a stent that is able to withstand the harsh mechanical aspects of the periphery often will not supply enough radial force to open the vessel satisfactorily. In many cases, medical practitioners desire the ability to combine endovascular clearing procedures with stenting. Such stenting may occur prior to, after, or both before and after the endovascular clearing procedure.

Accordingly, a need remains for devices that allow for improved atherectomy devices that clear materials from body lumens (such as blood vessels) where the device includes features to allow for a safe, efficient and controlled fashion of shaving or grinding material within the body lumen while minimizing procedure times.

SUMMARY OF THE INVENTION

Devices and methods described herein provide debulking devices having improved means of clearing obstructions within body lumens, especially the vasculature. The features of the devices and methods allow for controlled removal of occlusive materials. In some variations, the methods and devices also have features to convey the materials away from the operative site without the need to remove the devices from the body lumen. Additional aspects include controlled rates of tissue removal as well as other safety features to prevent accidental cutting of the lumen wall. Although the devices and methods described herein discuss removal of materials from a blood vessel, in certain cases the devices and methods have applicability in other body lumens as well. It should be noted that the variations and features of the devices described below may be incorporated selectively or in combination with a basic device configuration that includes a flexible body having a cutter, where the cutter includes a housing and a cutter, where the housing and cutter are able to rotate relative to each other. Variations include a cutter that rotates within the housing, a housing that rotates about the cutter, and combinations thereof.

One variation of the device described herein includes a device configured to remove material from body structures. The device may be a vascular device and have the required structure and configuration to navigate tortuous anatomy. Alternatively, the device may be a cutter that has features that are desired when used in other parts of the anatomy.

In any case, such a device may include a catheter body having a proximal end and a distal end, a cutter assembly located at the distal end of the catheter body, the cutter assembly comprising a housing having at least one opening and a cutter having at least one cutting surface configured to rotate relative to the housing, where movement of the cutting surface relative to the vessel removes occlusive material, a rotating shaft extending through the catheter body and coupled to the cutter, the shaft having a proximal end adapted to couple to a first rotating mechanism, and a deflecting member extending along the catheter body, such that the deflection member can cause deflection of the cutter assembly relative to an axis of the catheter.

Devices of the present invention can also include cutting assemblies where the rotating a cutter rotatably located within a housing has a plurality of cutting edges located on both a near cutting portion and a far cutting portion, where the near cutting portion and the far cutting portion are spaced along an axis of the cutter and the far fluted cutting portion has fewer fluted cutting edges than the near fluted cutting portion, where on rotation of the cutter the fluted cutting edges remove material from the body lumen.

In another variation, a rotatable cutter can include a first plurality of cutting edges extending helically along the entire cutter, and a second plurality of cutting edges extending helically only along a portion of the cutter.

The cutters describe herein can be used with housings that have multiple openings along a wall of the housing. Alternatively, or in combination, a front face of the housing can be open. In some variations, the front edge of the open housing can be configured as a forward cutting surface.

Additional variations of the devices described herein can include a tapered, or conical dilation member located at a tip of the housing. The dilation member provides numerous benefits in addition to dilating material towards openings in a housing of a cutting assembly.

Variations of the devices can also include multiple cutting surfaces. For example, the multiple cutting surfaces may cut tangential to a rotational direction of a cutting head, in a forward direction as the cutting assembly moves distally, and/or in a rearward direction as the cutting assembly is withdrawn proximally. The multiple cutting surfaces can be located on a single cutting head, or may be located on a housing of the cutting assembly. In certain variations of the device, a housing of the cutting assembly may be fully open at a distal end to expose a cutting head. Such a design can incorporate additional safety features to prevent excessive damage to vessel walls.

Variations of the deflecting member may include steerable sheaths adapted to deflect in shape. The steerable sheath may be located internally to a catheter body of the device. Accordingly, the catheter body remains stationary while the sheath can rotate to move a cutting head in an arc about the target body passage.

In some variations the steerable sheath may include a deflecting wire extending through a portion of the sheath, such that axial movement of the deflecting wire deflects the sheath. The deflecting wire can be affixed to the cutter assembly, to a portion of the catheter body that extends out of the deflecting sheath, or to other parts of the device as needed.

The deflecting member can also include a pre-shaped mandrel, or tube where such features are slidable within or relative to the device to produce movement of the cutting head relative to an axis of the device. The devices described herein may have any number of features that allow for locking the device after it is articulated. This feature provides a consistent diameter when sweeping or navigating through the anatomy.

As discussed herein, some variations of the devices have the ability to articulate. This articulation allows for steering the device to the target site as well as creating a sweeping motion of tissue removal. Accordingly, a deflectable sheath used in the device can be rotatable about the catheter body, or about an axis of the catheter.

The devices described herein may have a cutter assembly having a portion of its housing having a curved surface and where the opening forms a plane across the curved surface such that as the cutting surface rotates across the opening, a portion of the cutting surface extends out of the housing through the opening. The cutter assembly may also have various other features as described below that improve the safety of the device as it is articulated while cutting. Furthermore the cutter may have a number of features to impel or drive cut tissue into the cutter assembly for eventual removal by one or more conveying members.

As noted, the devices described herein may have one or more conveying members that convey materials and/or fluids through the device. Such a feature is useful to remove cut tissue and debris from the site during the procedure. In some variations, the device may include multiple conveyors to deliver fluids and remove debris. However, the devices of the present invention may also have containers for use in capturing debris or other materials generated during the procedure.

Another feature for use with the inventions herein is the use of a grinding burr rotatably coupled to a tip of the device. The burr can be useful to remove tissue that is otherwise not conducive to cutting with the cutter assembly.

In another variation, the invention may comprise a device having a straightening tube, with a straight distal portion, a catheter body having a proximal end and a distal end, the catheter body having a flexible section located towards the distal end, such that when located in the straight distal portion of the straightening tube the flexible section is less curved, a cutter assembly located at the distal end of the catheter body, the cutter assembly comprising a housing having at least one opening and a cutter having at least one cutting surface configured to rotate relative to the housing, where movement of the cutting surface removes material, and a rotating shaft extending through the catheter body and coupled to the cutter, the torque shaft having a proximal end adapted to couple to a first rotating mechanism.

In such a case, placement of the straight distal portion over the catheter allows for manipulation of the degree of curvature of the catheter. This feature allows for steering of the device.

As described herein, such a device may have the ability to sweep over an arc to deliver a larger cutting diameter than the diameter of the cutter assembly.

The devices described herein may use a guidewire for advancement through the body. In such cases the devices will have guide-wire lumens located within or about the catheter. Alternatively, a guide-wire section may be affixed to a portion of the device.

Devices of the present invention typically include a torque shaft to deliver rotational movement to components in the cutter assembly. Alternatively, a torque shaft or other such assembly may be used to produce the sweeping action described herein. In any case, the torque shaft may include one or more lumens. Alternatively, the torque shaft may be a solid or hollow member. Variations of the torque shaft also include those aspects known in catheter-type devices such as counter-wound coils, stiffening members, etc. In some variations, the torque shaft may have the conveying member integrally formed about the exterior or an interior surface of the shaft. Alternatively, or in combination, the conveying member may be placed on (or within) the torque shaft as described herein.

The invention also includes various methods of debulking material within body structures. These structures include occluded blood vessels (whether partially or totally occluded), various organs, cavities within the body, or other body lumens.

In one variation a method includes inserting a catheter body having a cutter assembly within the blood vessel, rotating the cutter assembly to remove the material and form a first opening in the body lumen, deflecting the first cutter assembly relative to an axis of the catheter body, rotating the deflected catheter tip while rotating the cutter assembly to form a second opening in the body lumen where the second is larger than the first opening.

The methods may include the use of any of the devices or features of the devices described herein. For example, the methods may include debulking occlusive material within a totally or partially occluded blood vessel by positioning a guidewire adjacent to the occlusive material in the blood vessel, feeding a debulking device on the guidewire to the occlusive material, the debulking device having a cutter, where the cutter includes a housing having a plurality of openings located about the housing and containing a rotatable cutter configured to cut the occlusive material through the openings, where the debulking device further includes a conical dilator tip located at a front of the housing, rotating the rotatable cutter, dilating the occlusive material away from the guidewire and towards an opening in the housing by inserting the conical tip into the occlusive material, and debulking the occlusive material after dilating the occlusive material by cutting the occlusive material with the rotatable cutter through the opening in the housing.

In an additional variation, the methods include circulating fluid for contrast to better visualize the obstruction.

As noted herein, combinations of aspects of the devices, systems, and methods described herein may be combined as needed. Furthermore, combinations of the devices, systems and methods themselves are within the scope of the disclosure.

BRIEF DESCRIPTION OF THE DRAWINGS

FIGS. 13A-13B show a control system for rotating and articulating the cutter assembly;

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1A:
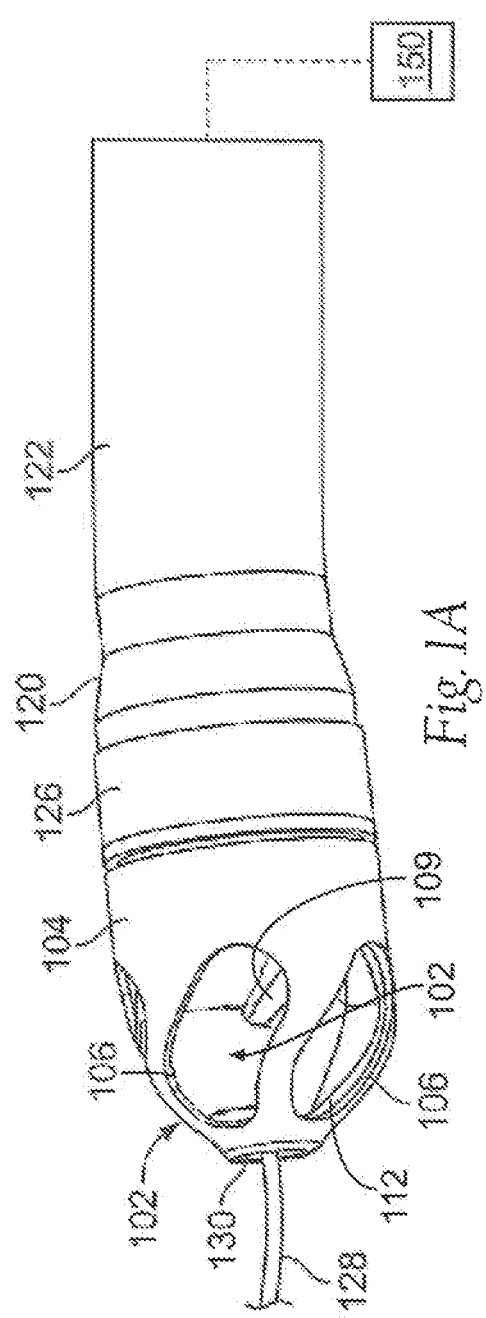
FIG. 1A illustrates an exemplary variation of a device according to the present invention.

FIG. 1A illustrates an exemplary variation of a device 100 according to the present invention. As shown the device 100 includes a cutter assembly 102 affixed to a catheter or catheter body 120. The catheter body 120 can be a reinforced sheath (e.g., a polymeric material with a braid). As shown, the catheter body may be optionally located within an outer sheath 122. It is noted that the cutter assembly shown in the figures exemplary purposes only. The scope of this disclosure includes the combination of the various embodiments, where possible, as well as the combination of certain aspects of the various embodiments.

FIG. 1A shows a variation of a cutter system or debulking device 100 where the cutter assembly 102 is within the housing 104. The cutter assembly contains a first set of cutting edges 112 and a second set of cutting edges 109, where the first cutting edges 112 extend along the entire length of the cutting assembly 102 (i.e., the entire length that is exposed in the openings 106 of the housing 104). In contrast, the second set of cutting edges 109 (in the figure only one such second cutting edge is visible).

Figure 1B:
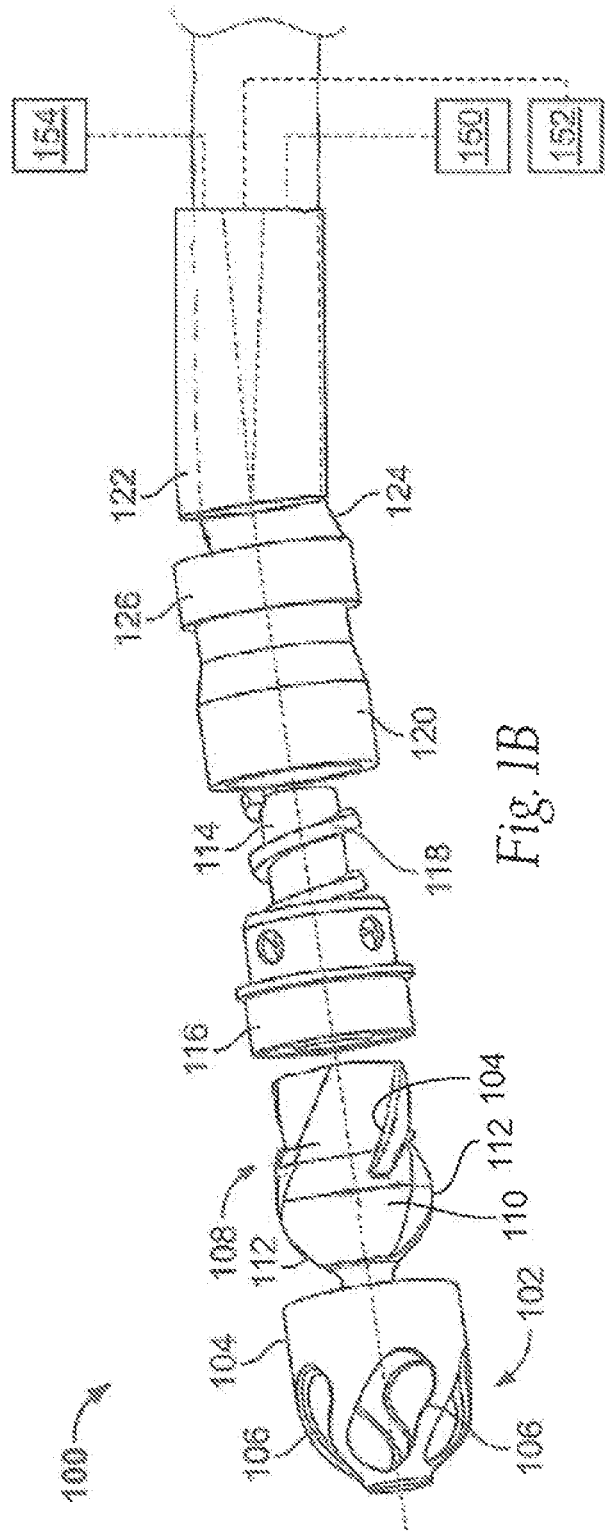
FIG. 1B shows an exploded view of the device of FIG. 1A.

FIG. 1B illustrates an exploded view of the device 100 of FIG. 1A. As shown, in this variation the cutter assembly 102 includes a cutter 108 is located within a housing 104. This cutter 108 includes a plurality of cutting edges 109 and 112. In this variation, the cutting edges comprise a first set of cutting edges 112 that extend along (or substantially along) the cutter 108 and a second cutting edge 109 that extends only along a portion of the cutter 108. Although the number of cutting edges can vary, typically the cutting edges will be symmetric about an axis 111 of the cutter 108. For example, in one variation, the illustrated cutter 108 will have a pair of second cutting edges 109 symmetrically located about the cutter 108 and a pair of first cutting edges 112 symmetrically located about the axis 111 of the cutter 108. Accordingly, such a construction results in two cutting edges 112 located on a far or distal end of the cutter 108 and tour cutting edges 109 and 112 located on a near or proximal end of the cutter 108.

Providing a cutter 108 with fewer cutting edges on a first cutting portion and an increased number of cutting edges on a second cutting portion, as shown, allows for a more aggressive cutting device. As illustrated in the figures, the cutter can be configured with cutting edges 109, 112 that are adjacent to grooves, channels, or flutes (where the combination is referred to as a "cutting flute"). The flute provides a path for the cut material to egress from the treatment site through the debulking device. By reducing the number of flutes on a far end of the cutter, the flutes can be made deeper. The deeper flutes allow the cutting edge adjacent to the flute to remove greater amounts of material. However, increasing the size of the material can also increase the chances that the material becomes stuck or moves slowly through the catheter during removal. To alleviate this potential problem and increase the efficiency of transporting the material through the catheter, the cutter can be configured with an increased number of cutting edges towards a rear of the cutter that reduce the size of the cut material.

Turning back to FIG. 1B, variations of the debulking device 100 can also include a cutter assembly 102 including a housing 104 with a plurality of openings 106 in a sidewall of the housing 104. However, additional cutter assembly configurations (as noted below) are contemplated. For example, and as noted below, other distinct embodiments of debulking devices a housing can include an opening in a front surface of the housing. In any case, many aspects of either system are combinable where such combinations are not inconsistent.

FIG. 1B also shows the cutter coupled to a rotating mechanism 150. In this variation the rotating mechanism couples to the cutter via a torque shaft 114 that transmits rotational energy from the rotating mechanism 150 (e.g., an electric, pneumatic, fluid, gas, or other motor) to the cutter 108. Variations of the devices include use of a rotating mechanism 150 located entirely within the body of the device 100. In one variation, the rotating mechanism 150 may be outside of the surgical field (i.e., in a non-sterile zone) while a portion of the device (e.g., the torque shaft—not shown) extends outside of the surgical field and couples to the rotating mechanism. The rotating mechanism can be a motor drive unit. In one working example, a motor drive unit having 4.5V and capable of producing cutting speeds up to 25K rpm was used.

FIG. 1B also shows a variation of the device 100 as having a deflecting member 124. In this variation the deflecting member 124 comprises a curved or curveable sheath/tube that causes deflection of the catheter body 122 when the sheath 124 advances distally. In alternate variations, the deflecting member can be a tendon, pull wire, tube, mandrel that causes a distal end of the catheter body to deflect. As described in detail below, the devices 100 can have deflecting members for articulate the cutting head and allow for a sweeping motion or orbital of cutting around an axis of the body lumen or within a space within the body.

In another variation, the device 100 can include a catheter body that comprises a soft or flexible portion. In one variation, this soft or flexible portion may be on a single side of the device 100 to allow flexure of the device 100 to articulate the cutting head. The flexure may be obtained with the deflecting members discussed above, or other means as known to those skilled in the art. In the illustrated variation, the deflecting member 124 comprises a sweep sheath. The sweep sheath 124 has a curved or shaped distal portion, where the curve may be planar or the shaped portion may be a non-planar shape). The distal portion of the sweep sheath is more flexible than a proximal portion of the catheter body. As a result, when the sweep sheath assumes a somewhat straightened shape when in the proximal portion of the catheter body. However, the distal portion of the catheter body is more flexible than the sweep sheath. Accordingly, once the sweep sheath is advanced into the distal portion of the catheter, the catheter assumes the shape or profile of the sweep sheath. This is a way to deflect the cutter assembly off the axis of the catheter. Rotation of the sweep sheath causes the movement of the cutter assembly to sweep in an arc and create an opening larger than a diameter of the catheter itself.

The device 100 may also include a vacuum source or pump 152 to assist in evacuation of debris created by operation of the device. Any number of pumps or vacuum sources may be used in combination with the device. For example, a peristaltic pump may be used to drive materials from the device and into a waste container. FIG. 1B also shows the device 100 coupled to a fluid source 154. As with the rotating mechanism, the vacuum source and/or fluid source may be coupled to the device from outside the surgical field.

It may be advantageous to rotatably couple the torque shaft to the drive unit electromagnetically, without physical contact. For example, the torque shaft 114 can have magnetic poles installed at the proximal end, within a tubular structure that is attached to the sheath around the torque shaft. The stationary portion of the motor can be built into a handle that surrounds the tubular structure. This allows the continuous aspiration through the sheath without the use of high speed rotating seals.

The device may also include a ferrule 116, as shown in FIG. 1B, that permits coupling of the catheter body 120 to the cutter assembly 102. The ferrule 116 may serve as a bearing surface for rotation of the cutter 108 within the cutter assembly 102. In the illustrated variation, the torque shaft 114 rotates inside the outer catheter body 120 and ferrule 116 to rotate the cutter and pull or aspirate tissue debris in a proximal direction. The clearance between the catheter tube and conveying member 118, as well as the pitch and thread depth of the conveying member 118, are chosen to provide the desired pumping effectiveness.

In one variation of the device, the housing 104 is connected to the catheter body 120 via the ferrule 116 and thus is static. The cutter 108 rotates relative to the housing 104 such that the cutting surface 112 on the cutter 108 shears or cleaves tissue and trap the tissue inside the housing 104 so that it can be evacuated in a proximal direction using the impeller action of the helical flutes and vacuum from the torque shaft. In alternate variations, such as where the housing includes a forward cutting surface, the housing 104 rotates as well as the cutter. Accordingly, the ferrule can serve as a bearing surface for both the housing and cutter.

The ferrule 116 can have a distal bearing surface to bear against the proximal surface of the cutter 108 and keeps the cutter axially stable in the housing 104. In cases where the housing is stationary, the ferrule 116 can be rigidly bonded/linked to the housing 104 using solder, brazing, welding, adhesives (epoxy), swaging, crimped, press-fit, screwed on, snap-locked or otherwise affixed. As shown, the ferrule 116 can have holes or other rough features that allow for joining with the catheter body. While adhesives and heat fusing may be employed in the construction, such features are not required. Often adhesives are unreliable for a small surface contact and heat fusing can cause the tube to degrade. The use of a mechanical locking ring 126 allows the cutting assembly 102 to be short. Such a feature is important for maximizing the flexibility of the distal section of the catheter as it is required to navigate tortuosity in blood vessels. In one variation, a ring or band (not shown) can be swaged onto the catheter body 120 and over the ferrule. This drives portions of the ring/band as well as the catheter body into the openings of the ferrule allowing for increased strength between the cutter assembly 102 and catheter body 120.

In another aspect of the invention, devices 100 can be adapted to steer to remove materials that are located towards a side of the body passage. Such devices may include a deflecting member that permits adjusting the orientation or offset of the cutter assembly 102 relative to a central axis of the device. In FIG. 1B, the deflecting member comprises a catheter 122 with a sweep sheath deflecting member 132 (however, the deflecting member can be a tendon, wire, tube, mandrel, or other such structure.) As described herein, other variations are within the scope of the device.

Figure 1C:
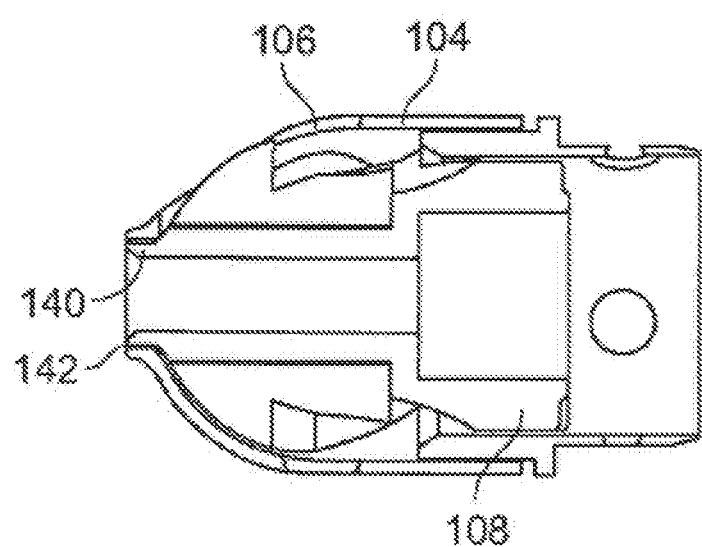
FIG. 1C shows a cross sectional view of the cutting assembly.

As shown in FIG. 1C, in certain variations, the housing 104 can have a distal nose with a center lumen 142 for receiving a mating piece 140 of the cutter 108. Such features assist in centering the cutter 104 concentrically inside the housing 104. As noted below, variations of the devices include the addition of a burr element (as shown below) for grinding hard tissue such as calcified plaque or a dilator member for separating materials towards the openings 106.

The geometry of the cutter 108 and housing 104 can be used to tailor the desired degree of cutting. The housing 104 and orientation of the openings 106 can be used to limit the depth of cutting by the cutter 108. In addition, the distal end of the housing 104 may be domed shaped while the proximal end may have a cylindrical or other shape. For example, by creating larger windows 106 in the housing a larger portion of cutter 108 may be exposed and the rate of cutting increased (for a given rotation speed). By placing the cutting window 106 on a convex portion or side wall of the housing, the debulking effectiveness is much less sensitive to the alignment of the cutter housing to the lesion, than if the window were on the cylindrical portion of the housing. This is a key performance limitation of traditional directional atherectomy catheters. In addition, placement of the window on the convex portion of the housing creates a secant effect (as described below).

Figure 1D:
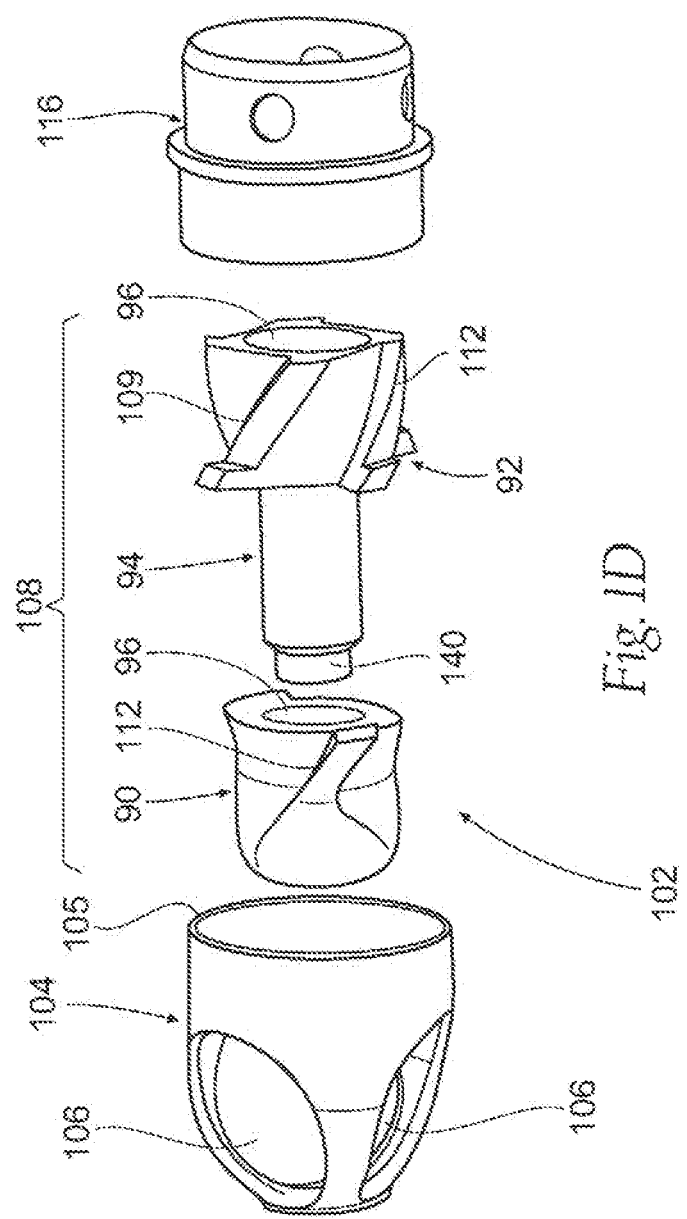
FIG. 1D shows an exploded view of the cutting assembly of FIG. 1A.

FIG. 1D illustrates an exploded view of a cutter assembly 102 and ferrule 116. In this variation, the cutter assembly 102 includes a housing 104 having three openings 106 symmetrically placed about a sidewall 105 of the housing. FIG. 1D also shows a variation of cutter 108 that comprises a far or distal portion 90 mounted on near or proximal portion 92 (where the near cutter portion can also be referred to as a cutter core adapter). The near cutter portion 94 contains a shaft terminating in a mating piece 140 for coupling the cutter 108 to the housing 104 (where the mating piece 140 nests within an opening in a front face of the housing 104. The cutter 108 can also include a passage 96 to allow for passing of a guidewire through the device.

Although the inventive device includes cutters formed from in a unitary body, providing the cutter 108 with far and near 90, 92 cutter portions allows for optimal selection of materials. In addition, as shown, a first cutting edge 112 can extend along both cutter portions 90, 92 while a secondary cutting edge 109 extends only along the near cutter portion 92. Given this configuration, when the cutter portions 90, 92 join to form the cutter 108 the far portion 90 of the cutter only contains two fluted cutting edges while the near cutting portion 92 includes four fluted cutting edges. Naturally, any number of fluted cutting portions are within the scope of the invention. However, variations include fewer cutting edges on a distal end of the cutter relative to the number of cutting edges on a proximal end of the cutter. Moreover, the cutting edges may or may not be symmetrically located about the cutter.

Figure 2A:
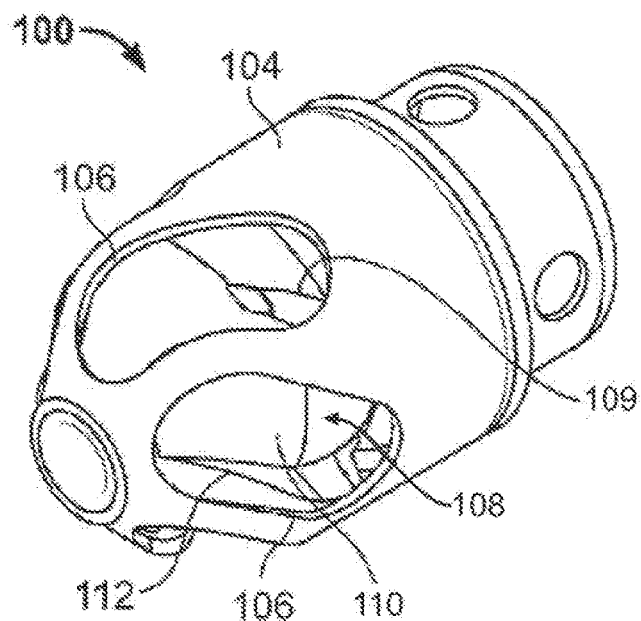
FIG. 2A shows the cutting edges through openings of a housing.

FIG. 2A illustrates an additional variation of the device 100 where the openings 106 may be helical slots that may or may not be aligned with the cutting edges 109, 112 of the cutter 108. For aggressive cutting, the slots 106 and cutting edges 109, 112 can be aligned to maximize exposure of the tissue to cutting edges. In other words, the cutting edges 109, 112 and openings 106 can be in alignment so all cutting edges 109, 112 are exposed at the same time to allow simultaneous cutting. Alternatively, alignment of the openings and edges 109, 112 may be configured so that fewer than all the cutting edges 109, 112 are exposed at the same time. For example, the alignment may be such that when one cutting edge is exposed by an opening 106, the remaining cutting edges are shielded within the housing 104. Variations of such a configuration allow for any number of cutting edges to be exposed at any given time. In addition, the variation depicted in FIG. 2A shows a window or opening 106 large enough to expose both the first 112 and second 109 cutting edges. However, in alternate variations, the windows can be configured to only expose the cutting edges 112 on the far end of the cutter 108.

In another variation, to even out the torque profile of the device when cutting, the cutter 108 can be configured such that the number edges/cutting surfaces 109, 112 of the flutes 110 that are aligned with the housing openings 106 does not vary throughout the rotational cycle. This prevents the catheter from being overloaded with torque spikes and cyclic torque variations due to multiple cutting edges/flutes engaging with tissue in synchrony. In other words, the length of the cutting surface 112 exposed through the openings 106 of the housing 104 remains the same or constant.

Figure 2B:
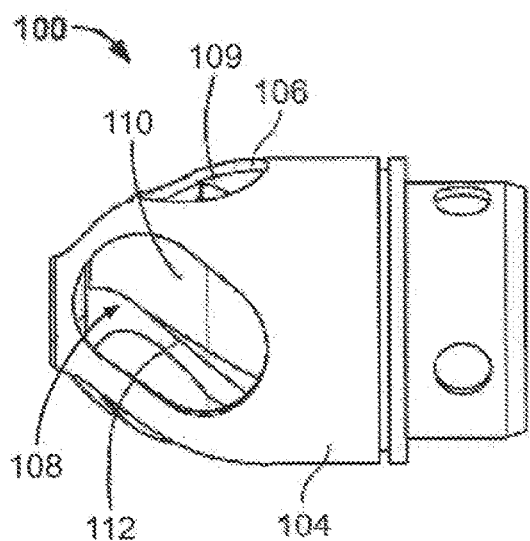
FIG. 2B shows a side view of the cutting assembly.

In the variation shown in FIG. 2B, the cutting edges 109, 112 are configured to capture debris within the flute 110 as the cutter 108 rotates. Typically, the cutter 108 may be designed with a secant effect. This effect allows for a positive tissue engagement by the cutter 108. As the cutter 108 rotates through the opening, the cutting edge moves through an arc, where at the peak of the arc the cutting edge slightly protrudes above a plane of the opening. The amount of positive tissue engagement can be controlled through selection of the protrusion distance through appropriate design of the housing geometry (for example, by a combination of location and size of the window and radius of curvature of the housing). The cutting edge 109 or 112 can extend out of the housing 104 through the window 106 as it rotates. This structure can also be designed to drive or impel the debris to the conveying member 118. In this case, the flutes 110 within the cutter 108 are helically slotted to remain in fluid communication with the conveying member 118. Variations of the device 100 can also include a vacuum source 152 fluidly coupled to the conveying member 118. In order to improve the impelling force generated by the cutters, variations of the cutter have helical flutes 110 and sharp cutting edges 112 that are parallel to each other and are wound from proximal to distal in the same sense as the rotation of the cutter. When the cutter rotates, it becomes an impeller causing tissue debris to move proximally for evacuation.

Figure 2C:
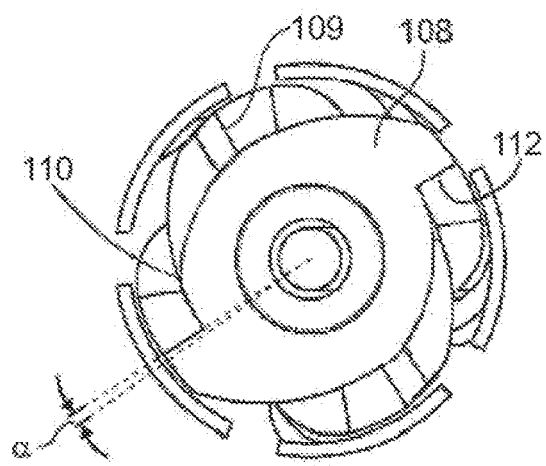
FIG. 2C illustrates a positive rake angle.

As shown in FIG. 2C, variations of the device may have cutting edges 109, 112 with positive rake angles α—that is the cutting edge is pointed in the same direction as that of the cutter rotation. This configuration maximizes the effectiveness of the impelling and cutting action (by biting into tissue and avoiding tissue deflection). The cutter is preferably made of hard, wear-resistant material such as hardened tool or stainless steels, Tungsten carbide, cobalt chromium, or titanium alloys with or without wear resistant coatings as described above. However, any material commonly used for similar surgical applications may be employed for the cutter. The outer surfaces of the proximal end of the cutter 108 are typically blunt and are designed to bear against the housing 104. Typically, these surfaces should be parallel to the inner surface of the housing.

FIGS. 2A-2B also show a surface of the cutter 108 having a curved-in profile distally and is close to the housing 104 surface. Note that housing openings 106 with this curved profile allows the cutting edge 112 to protrude beyond the housing's outer surface. In other words, the openings 106 form a secant on the curved surface of the housing 104. Such a feature allows improved cutting of harder/stiffer material like calcified or stiff fibrous tissue where such tissue does not protrude into the housing 104.

By controlling the number of cutting edges 109, 112 that are exposed through openings 106 in the housing 104, it is possible to control the relative amount of cutting engagement (both length of cutting and depth of cut, together which control the volume of tissue removed per unit rotation of the cutter). These features allow independent control of the maximum torque load imposed on the device 100. By carefully selecting the geometry of the flutes and or cutting edges 112 relative to the openings 106 in the housing, it is possible to further control the balance of torque. For example, the torque load imposed on the device is caused by the shearing of tissue when the cutter edge is exposed by passing through the housing window. If all cutter edges simultaneously shear, as for example when the number of housing windows is an even multiple of cutter edges, the torque varies cyclically with rotation of the cutter. By adjusting the number of cutters and windows so one is not an even multiple of the other (for example, by using 5 windows on the housing and 4 cutting edges on the cutter), it is possible to have a more uniform torque (tissue removal from shearing action) during each cycle of the cutter.

Figure 3A:
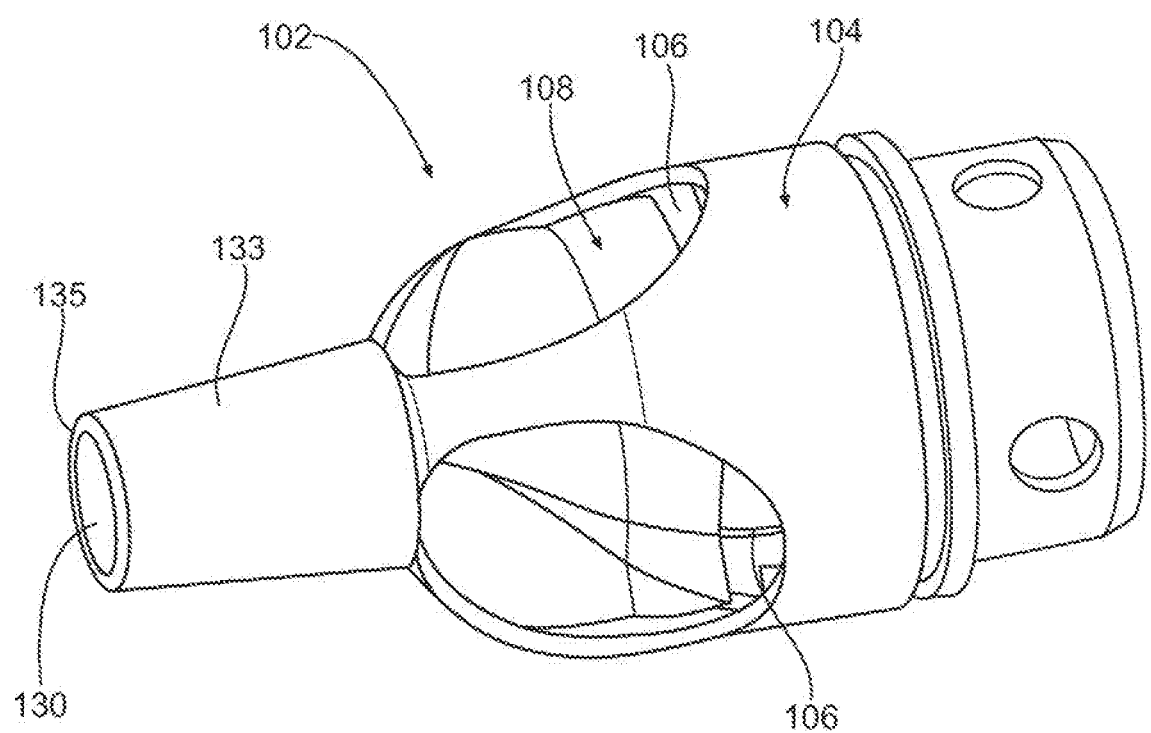
FIG. 3A illustrates a variation having a dilation member.

FIG. 3A shows a variation of a cutter assembly 102 where a housing 104 of the assembly 102 includes a conical, tapered, or dilator extension 133 extending from a front face of the housing 104. The dilator extension 133 serves a number of purposes namely that it can keep the cutting assembly 102 from damaging a vessel wall. In addition, the added structural reinforcement of the front face of the housing 104 reduces the chance that the rotating cutter 108 actually cuts through the housing 104. However, one important feature of the dilator extension 133 is that it provides a tapered surface from a guidewire to the openings 106 in the housing 104. Accordingly, as the dilator extension 133 advances through occlusive material, the dilator extension 133 forces or dilates material away from a guidewire towards the openings 106 and cutting edges. In order to dilate material away from a center of the device, the dilator extension 133 must have sufficient radial strength. In one example, the dilator extension 133 and housing 104 can be fabricated from a single piece of material as discussed herein.

The dilator extension 133 typically includes an opening 130 for passage of a guidewire. In addition, in most variations, a front end 135 of the dilator extension 133 will be rounded to assist in moving the occlusive material over a surface of the dilator 133. Furthermore, the surface of the dilator extension 133 can be smooth to permit sweeping of the cutting assembly 102 as discussed below. Alternatively, the dilator extension 133 can have a number of longitudinal grooves to direct material into the openings 106. In additional variations, the dilator extension 133 may not include an opening 130. In such a case, the dilator extension 133 would fully taper to a closed tip.

Figure 3B:
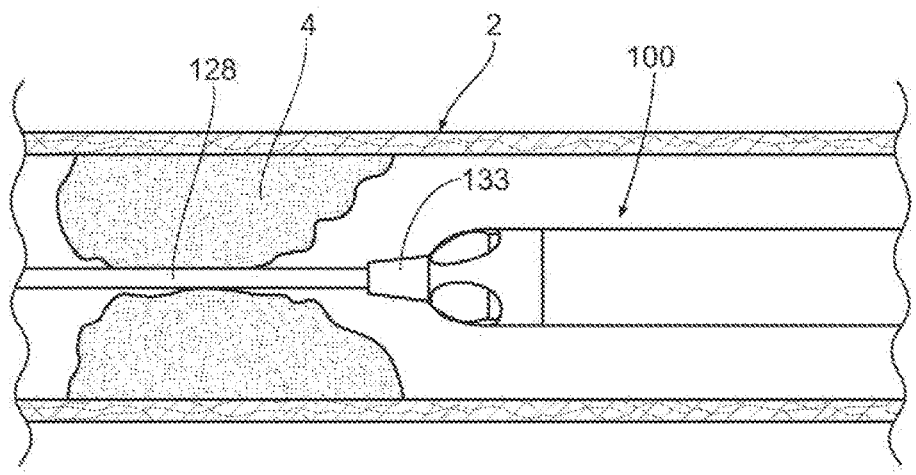
FIGS. 3B-3D show conceptually the use of a debulking device having a dilating member.
Figure 3C:
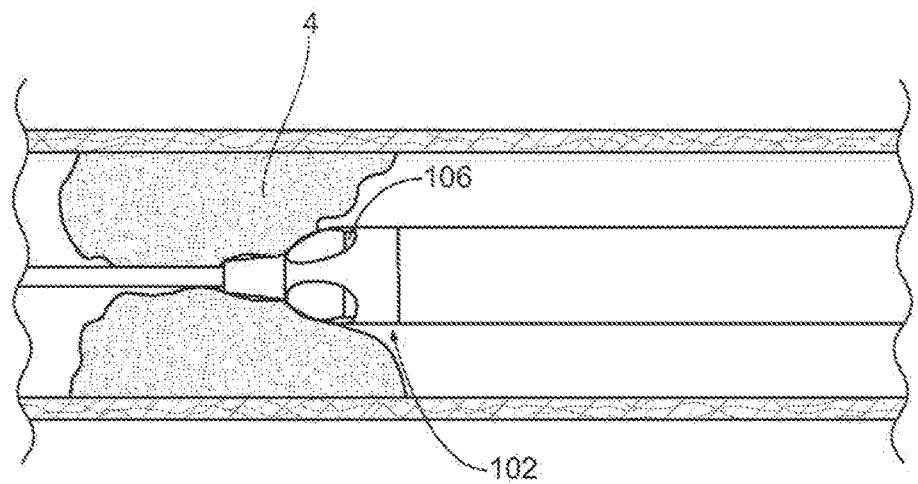
Figure 3D:
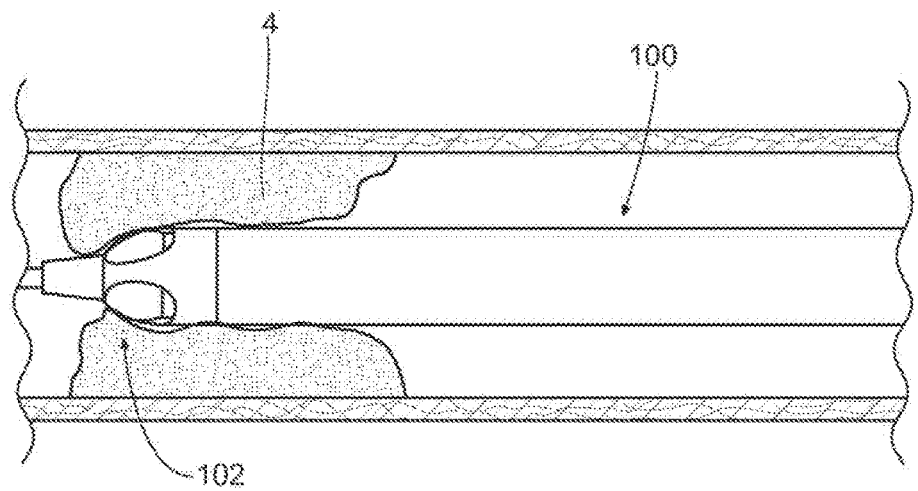

FIGS. 3B to 3D conceptually illustrate use of a debulking device having a dilating member 133. In this variation, the device 100 is advanced over a guidewire 128. However, use of a guidewire 128 is optional. As the device 100 approaches the plaque or occlusive material 4, the dilating member 133 forces the plaque 4 away from a center of the debulking device 100 and towards openings 106 in the cutting assembly 102 as shown in FIG. 3C. Clearly, the dilating member 133 must have sufficiently radial strength so that it forces the obstruction towards the openings 106. However, in those variations where the dilating member 133 is conical or tapered, the plaque material 4 is gradually moved towards the openings 106. In those devices not having a dilating member 133, the physician must apply excessive force to move the cutter against the plaque 4. In some excessive cases, the cutter actually shears through the housing leading to failure of the device. FIG. 3D illustrates a situation where the debulking device 100 traverses the entire occlusion 4. However, as noted below, the device may be configured for sweeping within the vessel. As such, the physician may choose to sweep the device 100 within the occlusion to open the occlusion during traversal of the occlusion or after a path is created through the occlusion. In either case, the nature of the dilation member 133 also functions to keep the cutting assembly 102 spaced apart from a wall of the vessel 2.

Figure 4A:
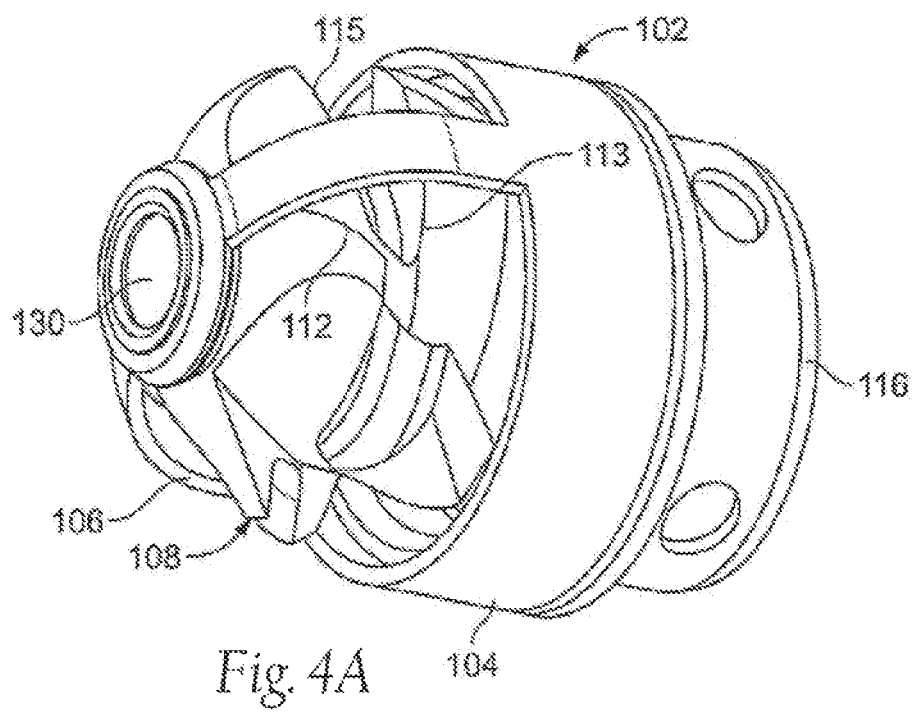
FIGS. 4A-4B show a variation of a shielded cutter having a plurality of front cutting surfaces, rear cutting surfaces, and fluted cutting surfaces.
Figure 4B:
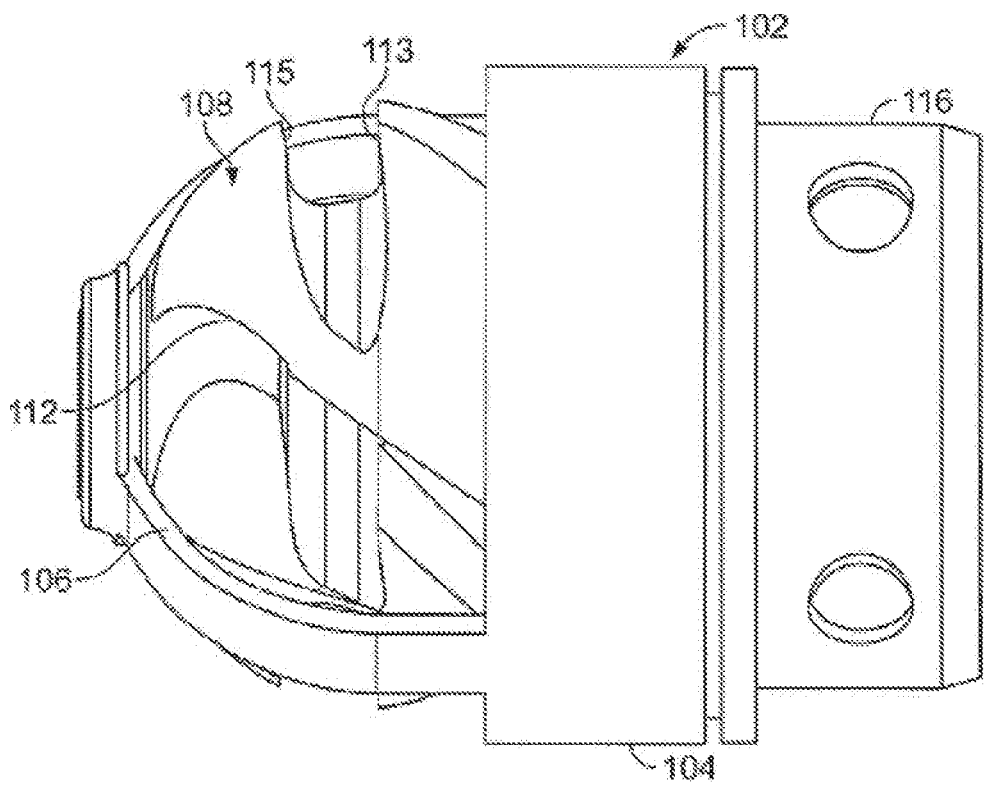

FIGS. 4A and 4B show an additional variation of a cutting assembly 102 for use with various debulking devices. FIG. 4B shows a side view of the cutter assembly 102 of FIG. 4A. In this example, the cutting assembly 102 includes larger windows 106 to accommodate a cutter 108 that includes a plurality of directional cutting surfaces 112, 113, 115. As the cutter 108 rotates within the housing 104, the fluted cutting edge 112 cuts in a direction that is tangential to a rotational direction of the cutter 108. In other words, the fluted cutting edges 112 cut material that is about the perimeter of the cutter 108 as it spins. The cutter 108 also includes on or more forward and rearward cutting surfaces 113, 115. These cutting surfaces 113, 115 engage tissue when the catheter is run in a forward direction or rearward direction. The ability to engage and remove engagements in the multiple directions have been shown to be important for effective debulking. However, a variation of a cutter 108 in the present invention can include a cutter 108 with one or two directional cutting surfaces. For example, the fluted cutting edges 112 can be combined with either the forward 113 or rearward 115 cutting surfaces. The ability to debulk in a forward, rearward and rotational directions also reduces the chance that the cutter assembly deflects from stubborn or hard tissue.

Figure 5A:
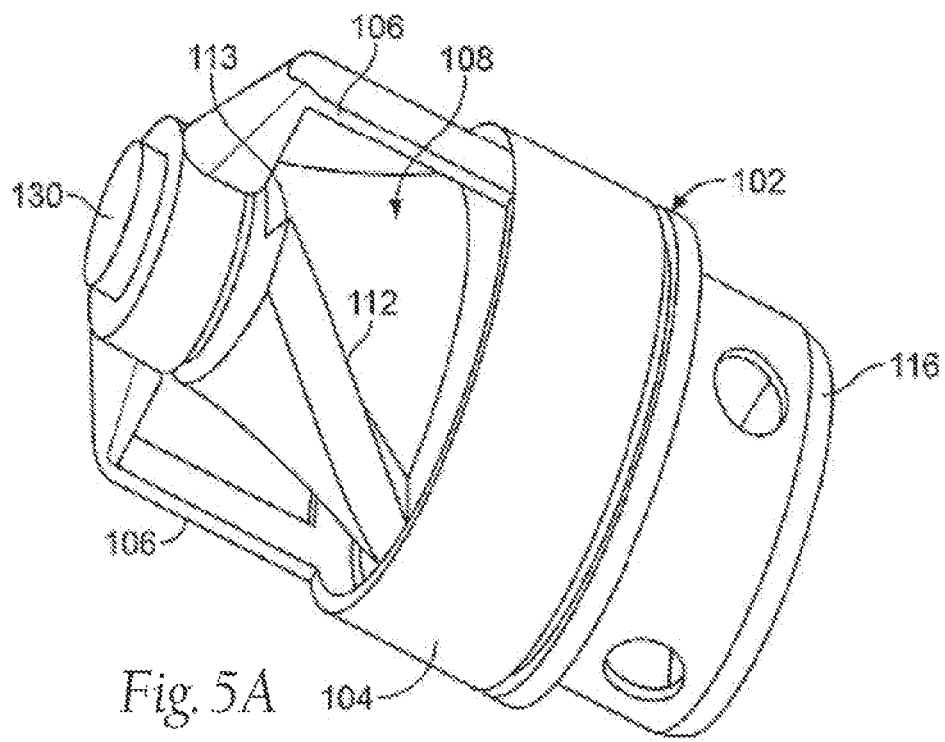
FIGS. 5A-5B show another shielded cutter having a plurality of front cutting surfaces and fluted cutting surfaces.
Figure 5B:
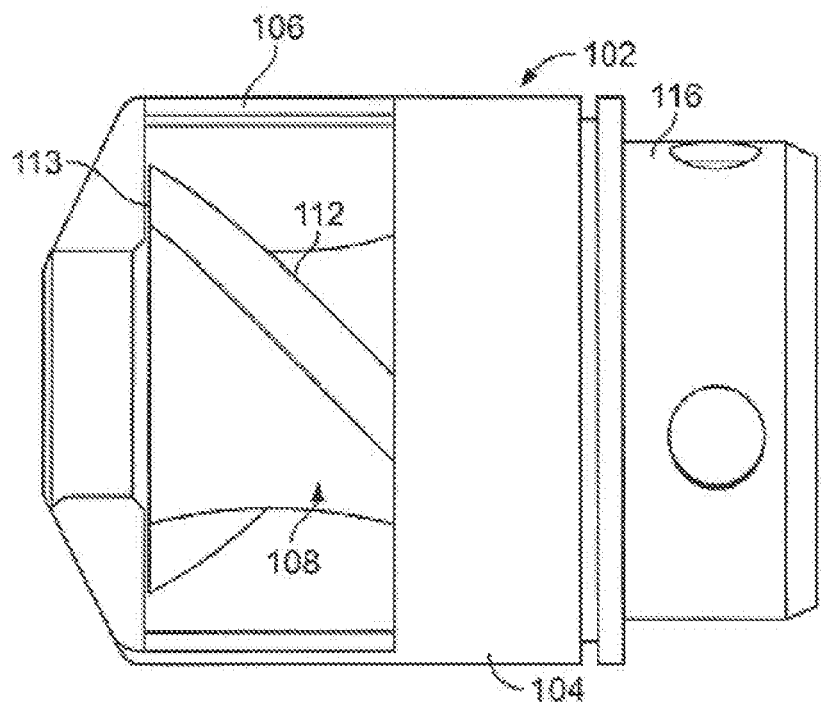

FIGS. 5A and 5B show another variation of a cutter assembly 102 having a forward cutting surface 113 on a front of the cutter 108. In this variation, the cutter housing 104 includes two large openings 106 that allow the forward cutting surface 113 to engage tissue when moved in a distal direction. The cutter 108 also includes a plurality of fluted cutting edges 112.

Figure 6A:
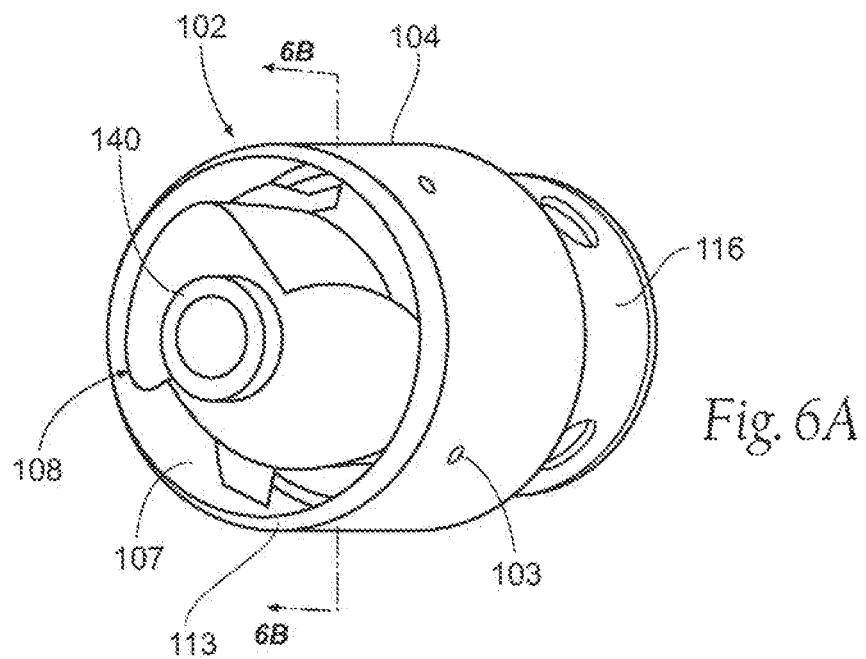
FIGS. 6A-6D show a cutter assembly having an open ended housing.
Figure 6B:
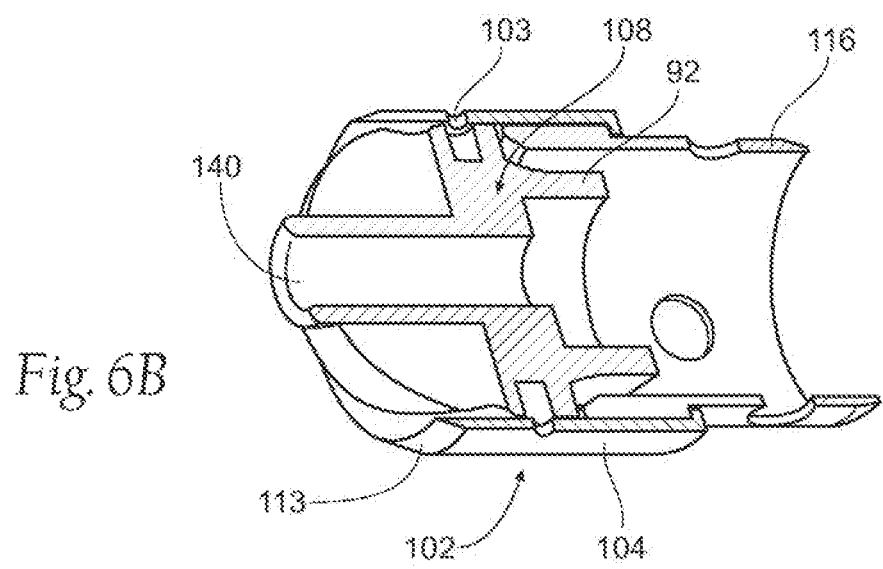
Figure 6C:
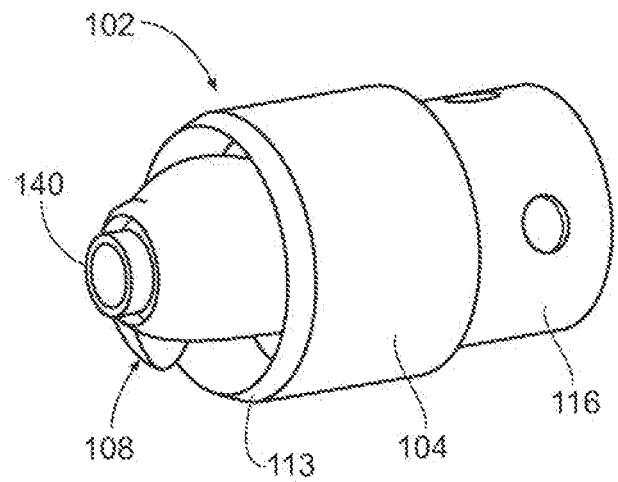

FIGS. 6A and 6C illustrates another variation of cutter assemblies 102 where the housing 104 includes an opening 107 located on a front face of a cylindrical housing 104. The cylindrical housing 104 containing a cutter 108 therein. In such a variation, the front edge of the housing 104 can function as a front or forward cutting surface. As shown, the front cutting surface 113 can be beveled on an outside surface of the housing 104. Such a beveled feature reduces the risk of the cutting surface 113 from gouging or otherwise damaging the wall of a vessel. As noted above, the forward cutting surface 113 engages and removes tissue or plaque 4 when the device is advanced in a distal direction within a body lumen 2 as shown in below. As discussed herein, features of the device, including a guidewire 128 assist in preventing the device from excessively cutting the lumen wall 2.

The cutter 108 construction can be similar to that shown above. Namely, where the cutter has a varying number of cutting edges on different portions. Alternatively, the cutter 108 can be a conventional fluted cutter. In one variation, the cutter 108 will be tapered or rounded such that the front of the cutter comprises a rounded or partial-ball shape.

The housing 104 can either be configured to rotate with the cutter 108 or can be stationary and function as a scraping, scooping, or chisel type surface. For example, FIGS. 6A and 6B show a variation where the housing 104 can be affixed to the cutter 108 allowing for rotation of the entire cutting assembly 102 about the catheter body (not shown) or ferrule 116. In the illustrated example, the cutting assembly 102 includes adjoining recessed pin cavities 103 for securing the housing 104 to the cutter 108. FIG. 6B shows a cross sectional view of the cutter assembly 102 of FIG. 6A. As illustrated, in this particular variation, the entire cutting assembly 102 rotates relative to the ferrule 116 which provides a bearing surface for the rotational housing 108. The proximal or near portion 92 of the cutter 108 rotates within the ferrule while the proximal end of the housing 104 rotates about the ferrule 116.

The housing 104 can be linked to the cutter 108 in a variety of ways as is well understood by those skilled in the art. For example the housing 104 can be directly linked or affixed to the cutter 108 via connection points 103 so that both rotate together. Alternatively, the housing 104 can be geared to rotate faster or slower than the cutter 108. In yet another variation, the gearing can be chosen to permit the housing 104 to rotate in an opposite direction than the cutter 108.

Variations of the cutting assemblies include cutters 108 that protrude partially from the forward cutting surface 113 of the housing 104. In other variations, the cutter 108 can extend further from the housing 104 or even cutters 108 that are totally recessed within the housing 108. In certain variations, it was identified that aligning the cutting surface 113 of the housing 104 with the deepest part of the flute on the cutter 108 allows for improved clearing of debris, especially where a single or double fluted cutting edge configuration is used on a distal portion of the cutter.

In any case, the fluted cutting edge 112 impels tissue debris back into the catheter. The outer diameter of the housing, proximal to the forward cutting surface 113 can be smooth to protect the lumen wall from the cutting action of the cutting edges. When the cutting assembly 102 is deflected, the outer diameter of the housing 102 becomes flush against the lumen wall and prevents the cutting edges from engaging the vessel wall. As the cutter assembly is advanced forward, it removes plaque 4 protruding from the lumen 2 wall and tissue debris is impelled backwards by the fluted edge 112 of the cutter 108.

Figure 6D:
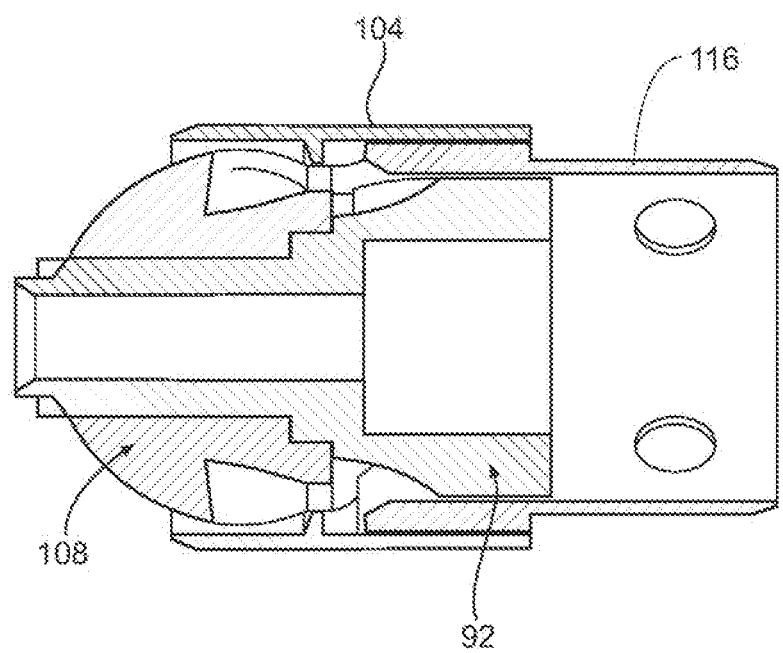

FIGS. 6C and 6D illustrate a variation of a cutting assembly 102 where a housing 104 of the cutting assembly 102 remains stationary about a catheter body (not shown) or ferrule 116 while the cutter 108 rotates within the ferrule.

FIG. 6D illustrates a partial cross sectional view of the cutting assembly 102 of FIG. 6C where the inner portion of the ferrule 116 provides a bearing surface for the proximal end 92 of the cutter 108. The housing 104 is affixed to the ferrule 116 and may also function as a bearing surface for the rotating cutter 108.

Figure 6E:
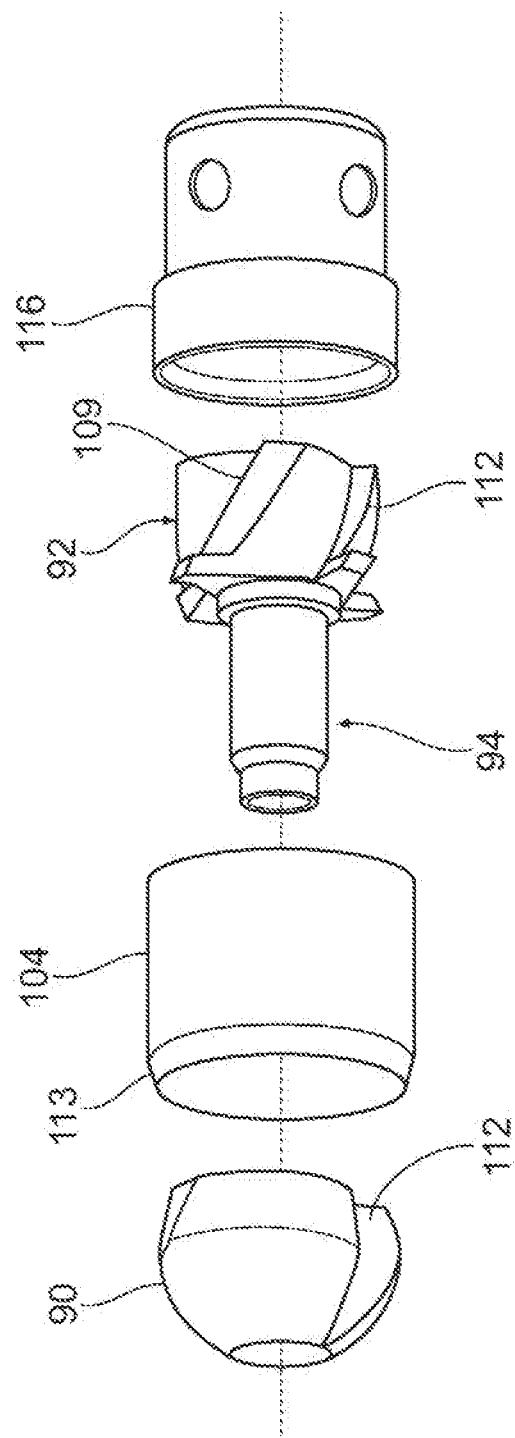
FIG. 6E shows an exploded view of the cutter assembly of FIG. 6C.

FIG. 6E shows an exploded view of the cutting assembly of FIG. 6C. Again, the cutter 108 can include a distal or far cutting portion 90 and a proximal or near cutting portion 92. The illustrated configuration provides a device having fewer cutting edges 112 on a distal portion 90 of the cutter and increased cutting edges 109 and 112 on a proximal cutting portion 92. However, variations include a traditional fluted cutter as well. The housing 104 is mounted about the cutter portions 90 and 92 and optionally secured to either the catheter body (not shown) or ferrule 116. As noted above, the housing 104 can also be affixed to the cutter so that it rotates with the cutter.

In alternate variations, the cutter assembly 102 the mating surface 140 can function as a blunt bumper at the very tip of the cutter 108 that acts as a buffer to prevent accidental cutting into the guidewire or the vessel wall given the cutter assemblies' open distal design. In additional variations, the housing 104 could be expandable (such as a basket or mesh). As the cutter 108 gyrates inside the housing, the housing expands to cut a larger diameter.

Figure 6F:
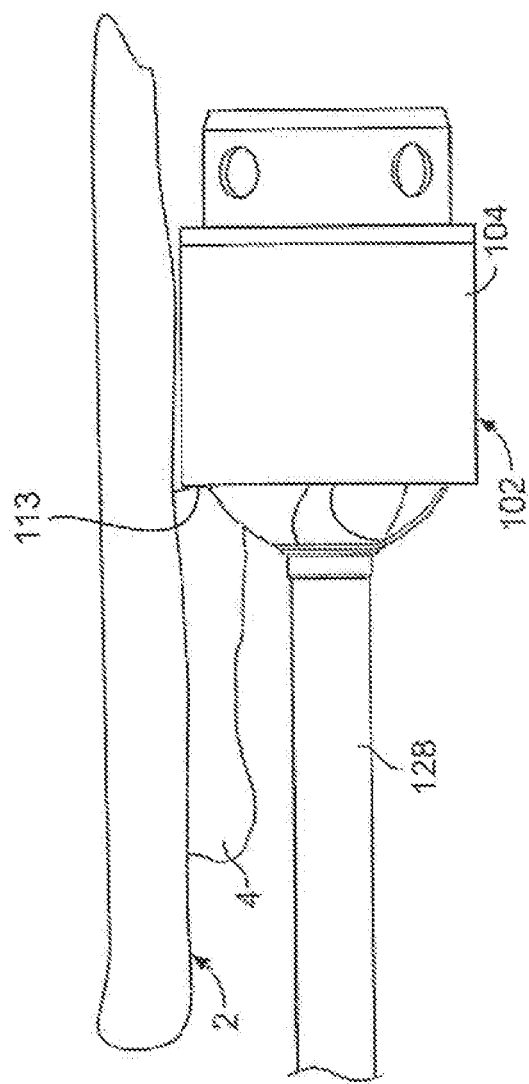
FIG. 6F shows a cutter assembly with the open ended housing removing material from a lumen wall.

FIG. 6F illustrates a cutting assembly 102 having a forward cutting surface 113 at a distal opening 117 of a housing 104. The housing 104 rotates along with the cutter 108 to assist in removal of tissue. As noted above, the forward cutting surface 113 engages and removes tissue or plaque 4 when the device is advanced in a distal direction within a body lumen 2 as shown in FIG. 5E. As discussed below, features of the device, including a guidewire 128 assist in preventing the device from excessively cutting the lumen wall 2.

The shielded atherectomy catheters described herein can perform biopsies, tumor removal, fibroid treatment, debulking of unwanted hyperplastic tissues such as enlarged prostate tissue, or other unwanted tissue such as herniated spinal disc material. The flexible, low profile catheter allows for ease of access to the treatment site and minimizes trauma or collateral damage to surrounding healthy tissue. With the continuous aspiration capability, contamination of the surrounding tissue during device introduction, treatment and removal is reduced or even eliminated. In addition, aspiration can be used to transfer biopsy tissue samples to outside the body for testing with the catheter remains in situ. This helps the physician make real time decision in advancing treatment of malignant, tissue. The shield on the cutter assembly maintains controlled excision of tissue by limiting the depth of cutter engagement and thereby prevents the physician from inadvertently cutting into healthy surrounding tissue. The tip steering capability of the cutter allows the physician to direct the cutter towards desired site of tissue removal and minimizing collateral tissue damage. Finally, by deflecting the cutter and rotating the deflection to sweep in an arc, the catheter can excise large tumors or tissue lumps larger than the diameter of the catheter. Thus, excision of large tumors can be achieved through a small access channel and thereby minimizing trauma to the patient.

The construction of the cutting assembly can provide for additional modes of energy delivery. For example, the catheter excises tissue in vascularized regions excessive bleeding can occur (e.g., lung biopsy and excision). Accordingly, energy can be delivered to the target site via a conductive cutter assembly (i.e. shield or even cutter). Sound energy (ultrasound), electrical energy (radio frequency current), or even microwaves can be used for this purpose. These energy sources delivered through the cutter can also be used to denature tissue (collagen), shrink tissue, or ablate tissue.

The cutter assembly can be made from a variety of materials. For example, the housing is preferably made of a strong, wear resistant material such as hardened steels, cobalt chromium, carbides or titanium alloys with or without wear resistant coatings like TiNi. In particular the use of coatings will allow the use of tool steels which, unless coated, do not have acceptable corrosion resistance and biocompatibility. The cutter or cutter can be fabricated from steel and can be coated with a titanium nitride. Alternatively, the cutter can be fabricated from a tungsten carbide material.

Coatings can be applied to the moving components in the catheter to reduce friction. In one embodiment, the sheaths and the torque shaft are coating with a hydrophilic coating (polyvinyl alcohol) to reduce friction between the moving components in the catheter. The coatings can also be hydrophobic (e.g. parylene, PTFE). The coatings can be impregnated with heparin to reduce blood clotting on surface during use.

Figure 7:
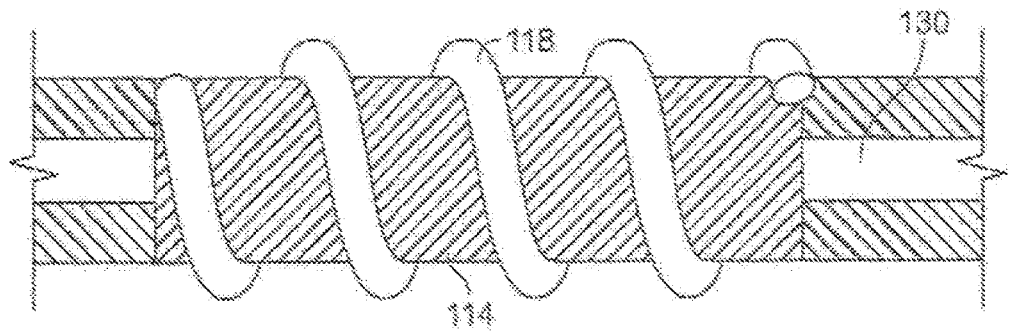
FIG. 7 shows a partial cross sectional view of a variation of a torque shaft having counter wound coils.

FIG. 7 shows a partial sectional view of an example of a torque shaft 114 that is coupled to a cutter assembly. To aid in removal of materials, the torque shaft can be a set of counter-wound coils, with the outer coil wound at the proper (greater) pitch to form the conveying member 118. Winding the coils counter to each other automatically reinforces the torque shaft 114 during rotation. Alternatively, the torque shaft 114 may be made out of a rigid plastic, rendered flexible by incorporation of a conveying member 118. Although the shaft may be fabricated from any standard material, variations of the shaft include a metal braid embedded in polymer (PEBAX, polyurethane, polyethylene, fluoropolymers, parylene) or one or more metal coils embedded in a polymer such as PEBAX, polyurethane, polyethylene, fluoropolymers or parylene. These constructions maximize torsional strength and stiffness, as well as column strength for "pushability", and minimize bending stiffness for flexibility. Such features are important for navigation of the catheter through tortuous vessels but allow for smooth transmission of torque over the long length of the catheter. In the multi-coil construction, the inner coil should be wound in the same sense as that of the rotation so that it would tend to open up under torque resistance. This ensures that the guidewire lumen remain patent during rotation. The next coil should be wound opposite the inner to counter the expansion to keep the inner coil from binding up against the outer catheter tube.

FIG. 7 also shows a torque shaft 114 having a central lumen 130. Typically the lumen will be used to deliver a guidewire. In such cases, the central lumen may be coated with a lubricious material (such as a hydrophilic coating or Parylene) or made of a lubricious material such as PTFE to avoid binding with the guidewire. However, in some variations a guidewire section is affixed to a distal end of the housing. Moreover, the central lumen of the torque shaft 114 may also be used to deliver fluids to the operative site simultaneously with the guidewire or in place of the guidewire.

Figure 8A:
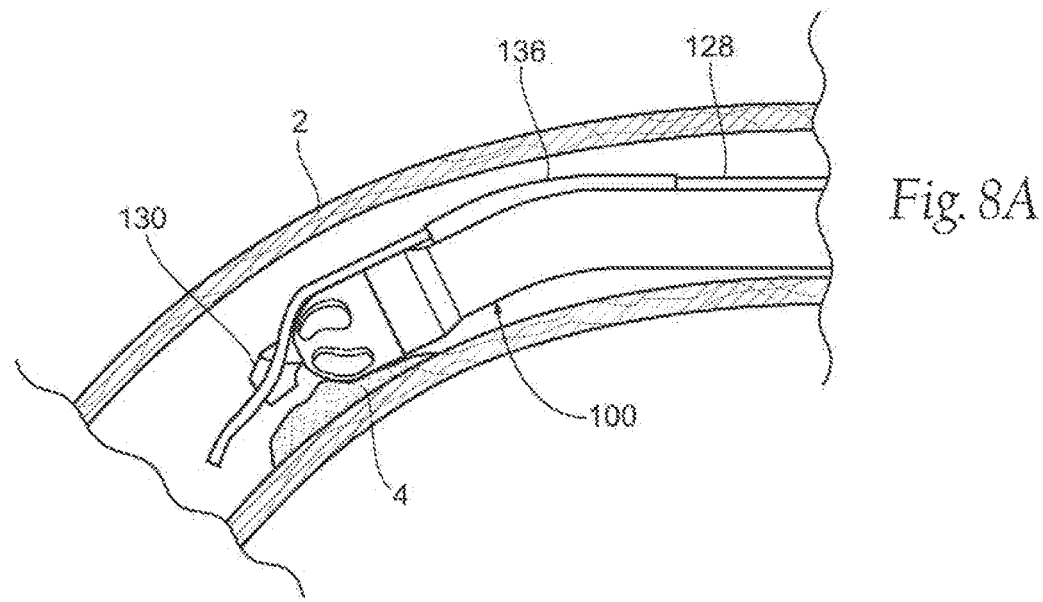
FIG. 8A shows a variation of a device configured for rapid exchange.

FIG. 8A illustrates a variation of a device 100 configured for rapid exchange. As shown, the device 100 includes a short passage, lumen, or other track 136 for the purpose of advancing the device 100 over a guidewire 128. However, the track 136 does not extend along the entire length of the device 100. Moreover, an additional portion of the track 136 may be located at a distal end of the catheter to center a guidewire 128.

This feature permits rapid decoupling of the device 100 and guidewire 128 by merely holding the guidewire still and pulling or pushing the catheter 100 over the guidewire. One benefit of such a feature is that the guidewire 128 may remain close to the site while being decoupled from the device 100. Accordingly, the surgeon can advance additional devices over the guidewire and to the site in a rapid fashion. This configuration allows for quick separation of the catheter from the wire and introduction of another catheter over the wire since most of the wire is outside of the catheter.

Figure 8B:
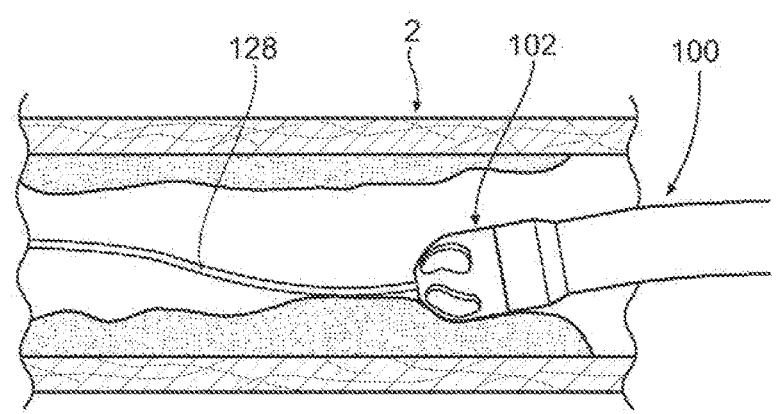
FIG. 8B illustrates an example of centering a tip of a cutting assembly over a guide wire.

As shown in FIG. 8B, centering the tip of the cutting assembly 102 over a guide wire 128 improves the control, access and positioning of the cutting assembly 102 relative to a body lumen or vessel 2. To accomplish this, the cutting assembly 102 can have a central lumen to accommodate a guide wire 128. Variations of the device 100 includes a central guide wire lumen runs the length of the catheter through all central components including the torque shaft and the cutter. As noted above, a guidewire 128 can be affixed to the housing 104 or other non-rotational component of the cutting assembly 102. In such a case, the guidewire 128 may preferably be a short segment that assists with navigation of the device through an occluded portion of a body lumen. However, the devices 100 can also operate without a guidewire since the head is steerable like a guidewire.

Figure 9A:
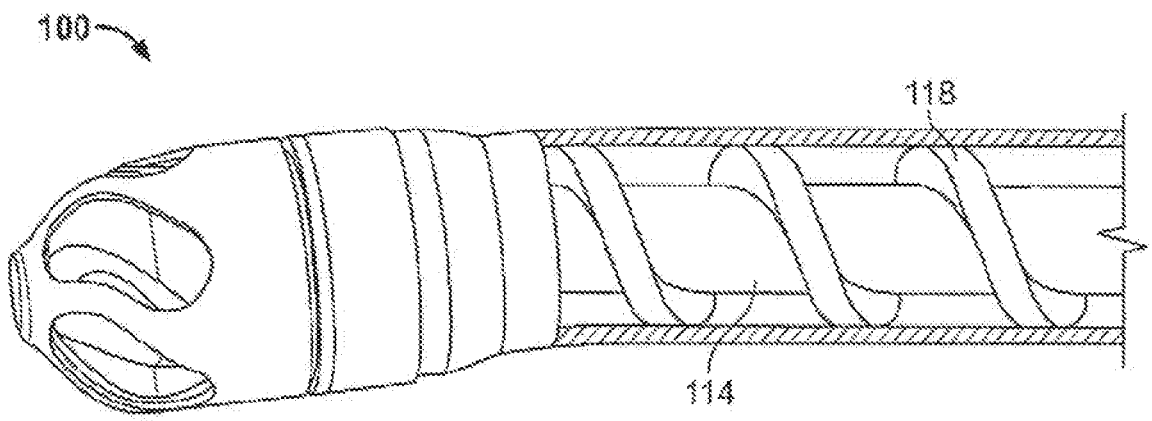
FIG. 9A shows a conveyor within the device.

FIG. 9A illustrates a partial cross-sectional view of another variation of a device 100. As shown, this variation of the device 100 includes a conveyor member 118 located within the device 100 and located on an exterior surface of a torque shaft 114. The conveyor member 118 may be an auger type system or an Archimedes-type screw that conveys the debris and material generated during the procedure away from the operative site. In any case, the conveying member 118 will have a raised surface or blade that drives materials in a proximal direction away from the operative site. Such materials may be conveyed to a receptacle outside of the body or such materials may be stored within the device 100. In one variation, the torque shaft 114 and conveying member 118 extend along the length of the catheter.

Figure 9B:
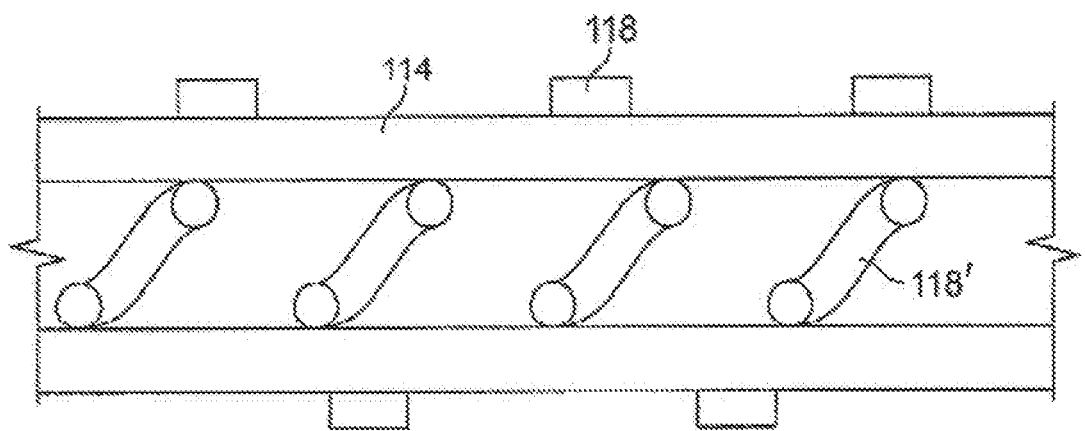
FIG. 9B shows a second conveyor within a torque shaft.

In some variations, the conveying member 118 may be integral to the shaft 114 (such as by cutting the conveying member 118 into the torque shaft 114 or by extruding the torque shaft 114 directly with a helical groove or protrusion. In an additional variation as shown in FIG. 9B, an additional conveying member 118 may be incorporated on an inside of the torque shaft, where the internal conveying member is wound opposite to that of the external conveying member 118. Such a configuration allows for aspiration and debris (via the external conveying member 118) and infusion (via the internal conveying member 118). Such a dual action can enhance the ability to excise and aspirate plaque by: (1) thinning the blood, whether by viscosity alone or with the addition of anti-coagulants such as heparin or warfarin (cumadin), and/or anti-platelet drugs such as Clopidegrel, (2) improving the pumpability (aspirability) of the excised plaque by converting it into a solid-liquid slurry that exhibits greater pumping efficiency, and (3) establishing a flow-controlled secondary method of trapping emboli that are not sheared directly into the housing, by establishing a local recirculation zone.

As noted above, the conveying member 118 can be wound in the same directional sense as the cutter 108 and in the same direction of rotation to effect aspiration of tissue debris. The impeller action of the cutter 108 moves the tissue debris from inside the housing 104 openings 106 into the torque shaft. The pitch of the cutting edges 112 may be matched in to that of the conveying member 118 to further optimize aspiration. Alternatively, the pitch of the conveying member 118 may be changed to increase the speed at which material moves once it enters the conveying member 118. As discussed herein, debris can be evacuated outside the body by the conveying member 118 action along the length of the catheter and with or without supplement of the vacuum 152 pump connected to the catheter handle. Alternatively, the debris may be accumulated in a reservoir within the device.

Figure 10A:
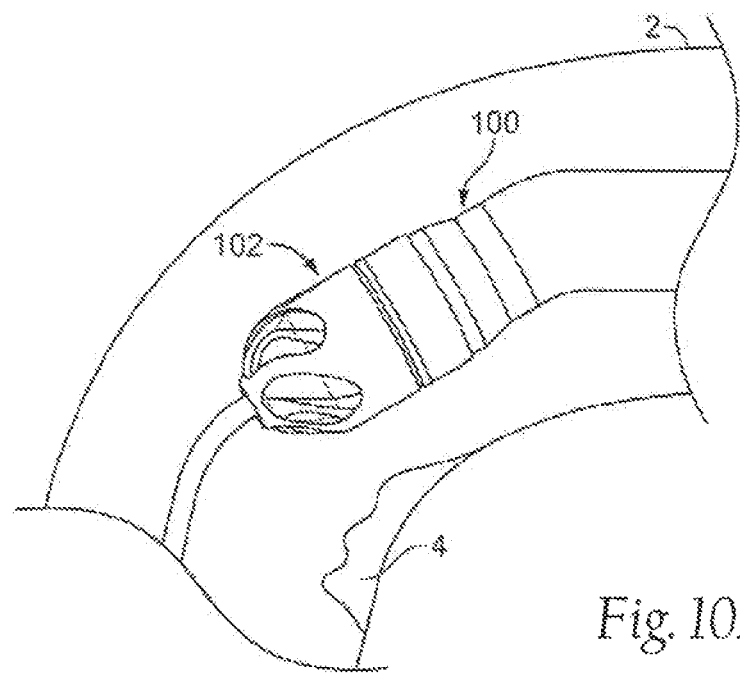
FIG. 10A illustrates articulation of a tip of the device.

FIG. 10A illustrates an example of a variation of a device 100 equipped to have an articulating or steerable cutter assembly 102. The ability to steer the tip of the device 100 is useful under a number of conditions. For example, when debulking an eccentric lesion as shown, the cutting assembly 102 should be pointed towards the side of the vessel 2 having the greater amount of stenotic material 4. Naturally, this orientation helps prevent cutting into the bare wall/vessel 2 and focuses the cutting on stenotic tissue 4. As shown in when in a curved section of the vessel 2, without the ability to steer, the cutting assembly 102 would tend to bias towards the outside of the curve. Steering allows the cutting assembly 102 to point inward to avoid accidental cutting of vessel wall 2.

Figure 10B:
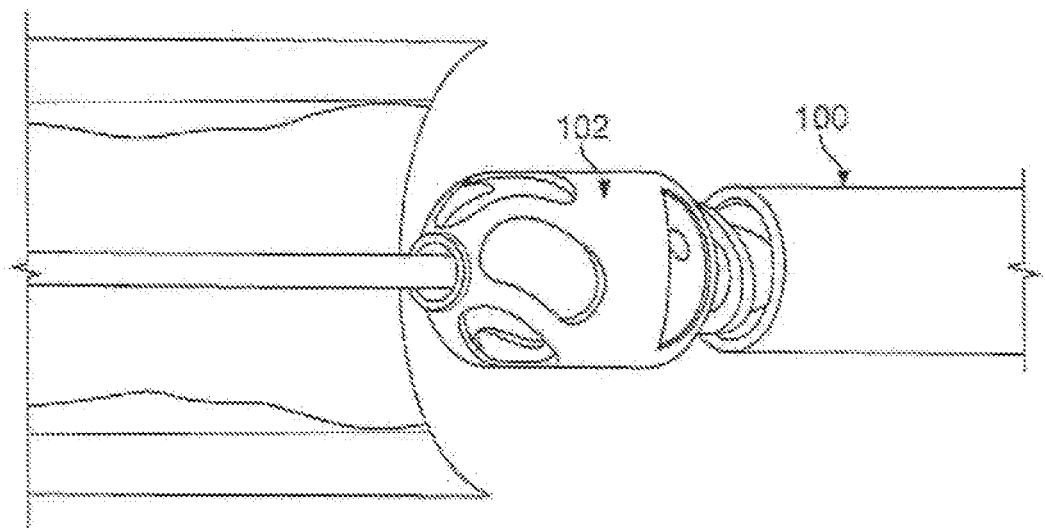
FIG. 10B-10D shows sweeping of the cutting assembly.
Figure 10C:
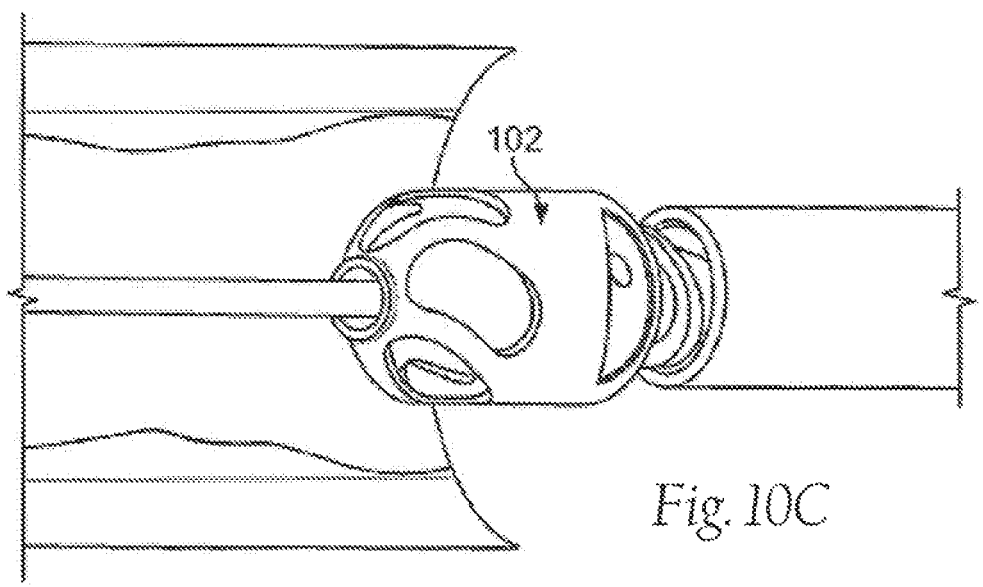
Figure 10D:
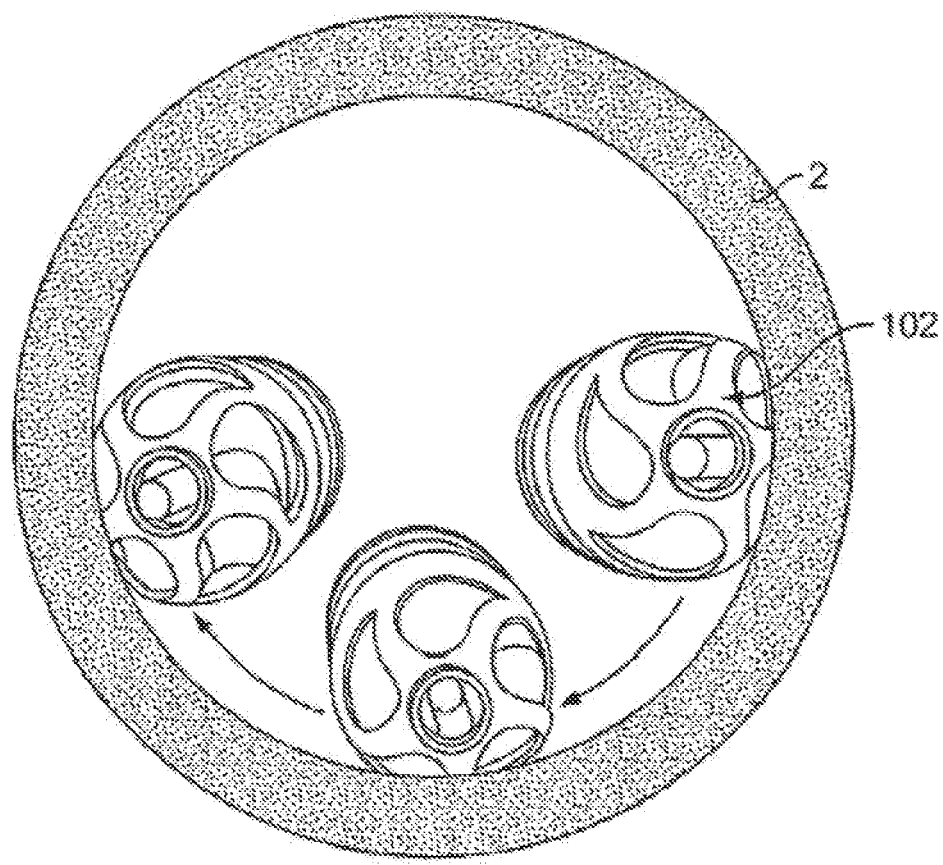

The ability to steer the device 100 also allows for a sweeping motion when cutting occlusive material. FIG. 10B shows the rotation of the cutting assembly 102. As shown in FIG. 10C, when the cutting assembly 102 deflects relative to the axis of the catheter, rotation of the deflected portion 102 creates a sweeping motion. It is noted that rotation or articulation of the cutting assembly also includes rotation or articulation of the catheter to allow the cutting assembly to deflect relative to an axis of the catheter. FIG. 10D shows a front view taken along an axis of the vessel to illustrate the sweeping motion causing the cutting assembly 102 to "sweep" over a larger region than the diameter of the cutting assembly. In most cases, when articulated, the device will be rotated to sweep over an arc or even a full circle. The rotation of the cutter may or may not be independent of the rotation of the device. A user of the device may couple the sweeping motion of the cutting assembly with axial translation of the catheter for efficient creation of a larger diameter opening over a length of the occluded vessel. The combination of movement can be performed when the device is placed over a guidewire, for example by the use of a lead screw in the proximal handle assembly of the device. In another aspect of the devices described herein, the angle of articulation may be fixed so that the device sweeps in a uniform manner when rotated.

A number of variations to control the deflection of the device 100 are described herein. For example, as shown in FIG. 1A the sheath 122 itself may have a pre-set curve. In such a case, the area of the catheter body 120 adjacent to the cutting assembly 102 will be sufficiently flexible so as to assume the shape of the curved sheath 122.

Figure 10E:
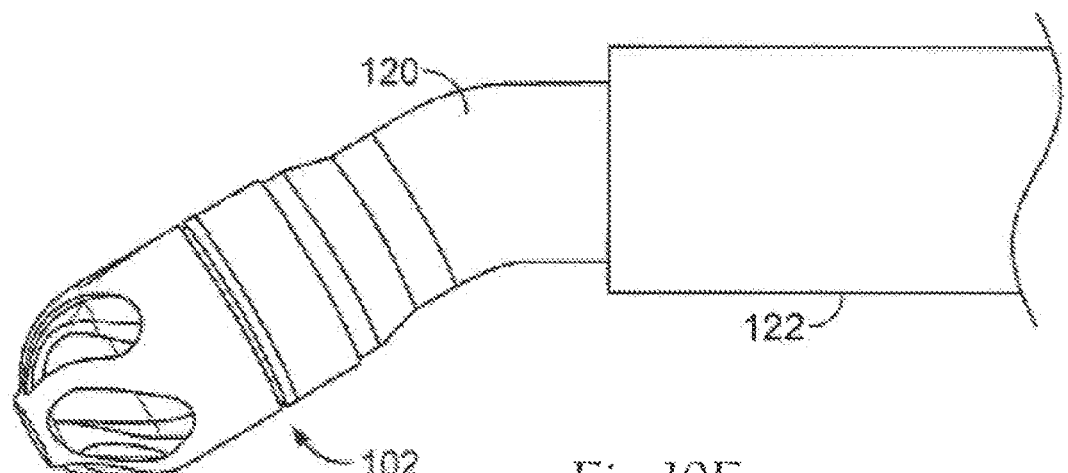
FIG. 10E illustrates another variation where the catheter body includes a set curve in an area that is adjacent to the cutting assembly.

FIG. 10E illustrates another variation where the catheter body 120 includes a set curve in an area that is adjacent to the cutting assembly 102. In this case, the outer sheath 122 can be made to be straight relative to the catheter body 120. Accordingly, advancement of the curved portion of the catheter body 120 out of the sheath 122 causes the catheter body 120 to assume its curved shape. The degree of articulation in such a case may be related to the degree of which the catheter body 120 is advanced out of the sheath 122.

Figure 11A:
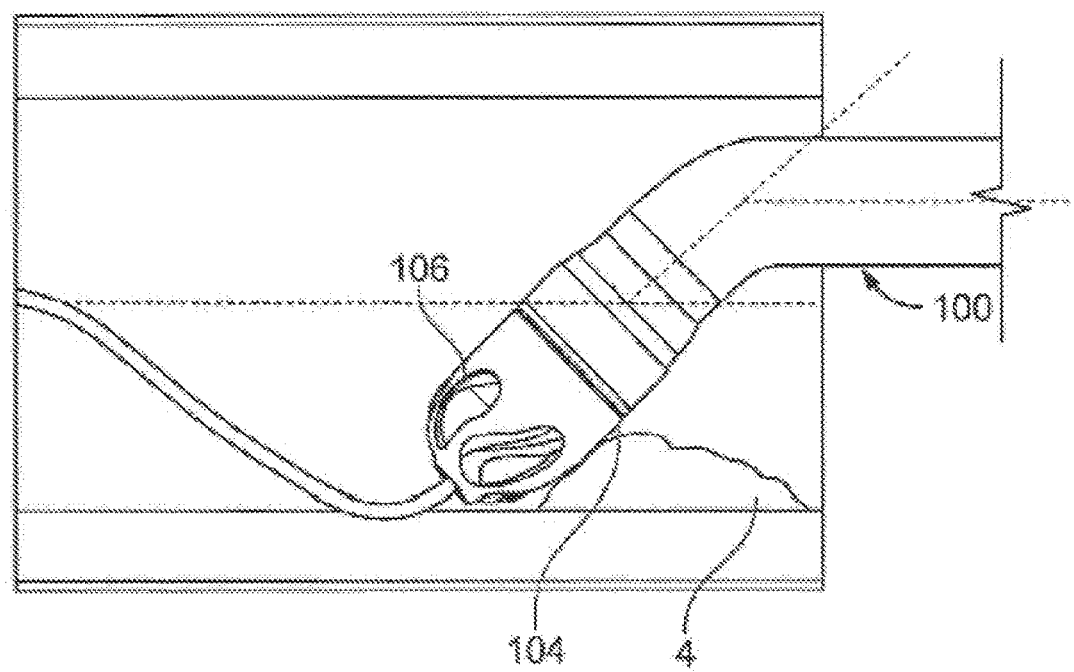
FIG. 11A shows placement of housing windows to prevent damage to the vessel walls.

In addition, the shape of the housing 104 as well as the location of the windows 106 can be chosen so that when the device 100 is substantially aligned with the lesion, or engages it at less than some critical attack angle, it will cut effectively. However, when pivoted at an angle greater than the critical angle, the cutting edges or grinding element will not engage the lesion as shown in FIG. 11A. This means that at large deflections, as the catheter tip approaches the vessel wall, it automatically reduces its depth of cut and ultimately will not cut when the critical angle is exceeded. For example, the cutter distal tip is blunt and does not cut. As the catheter tip is deflected outward, the blunt tip contacts the vessel and keeps the cutting edges proximal to the tip from contacting the vessel wall. Also the wire in combination with the device can also act as a buffer to prevent the cutting edges from reaching the vessel.

Figure 11B:
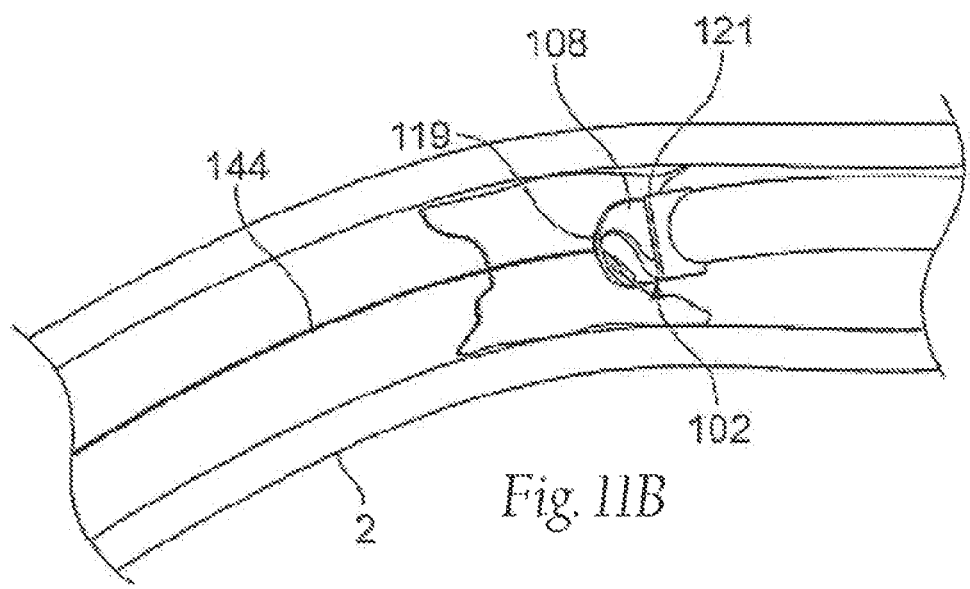
FIGS. 11B-11C shows placement of features of the cutter assembly that prevent damage to the vessel walls.
Figure 11C:
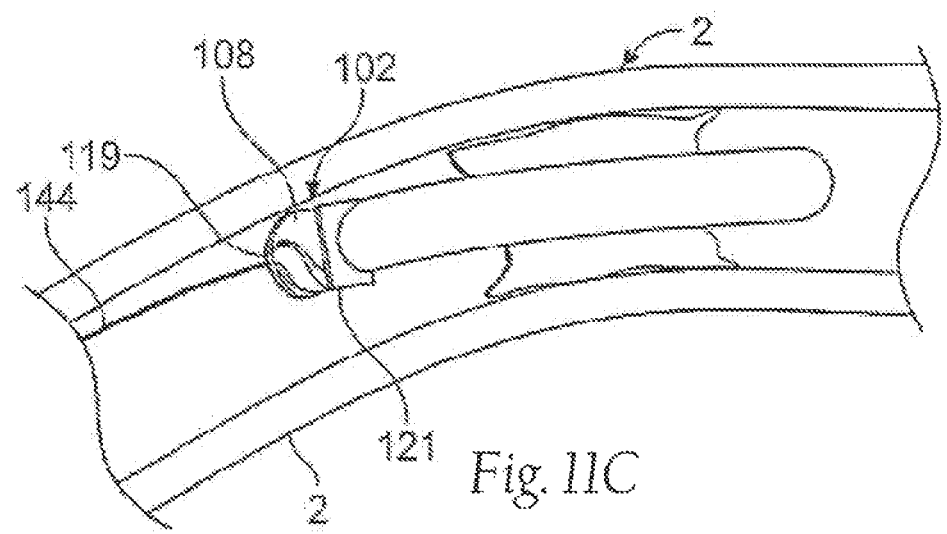

FIGS. 11B and 11C show a cutter assembly design that is specialized for forward cutting. This particular variation includes an open ended housing where the cutter extends from the housing (as shown above). However, a blunt bumper 119 at the tip of the cutter 10 acts as a buffer to prevent accidental cutting into the guidewire 144 or excessively into the lumen wall 2. In addition, this design can optionally incorporate a static housing portion 121 on a back end of the cutter assembly 102 that partially shields the cutter from deep side cuts into the lumen wall 2.

As mentioned above, variations of the device 100 allow directional control of the cutting assembly 102. In those variations where a slidable, torqueable sheath advances relative to the catheter body 122 (either external or internal to the catheter body) that can be flexed at the distal end. With the sheath flexed the catheter tip is pointed in the direction of the flex and the degree of bias is affected by the amount of flex on the sheath. The sheath can be rotated about the catheter or vessel long axis to change the direction of the cutting assembly. Also as noted above, this rotation can also effect a sweep of the cutting assembly 102 in an arc or a circle larger than a diameter of the cutter 102 (e.g. see FIG. 100). Such a feature eliminates the need to exchange the device for a separate cutting instrument having a larger cutting head. Not only does such a feature save procedure time, but the device is able to create variable sized openings in body lumens.

Figure 12A:
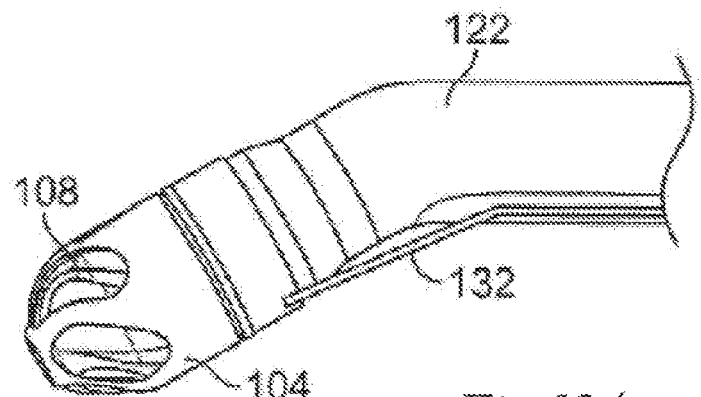
FIGS. 12A-12E show variations of the device for articulating the cutting assembly.

As shown in FIG. 12A, the tension on a slidable wire 132 in the wall of the sheath 122 can cause flexure of the sheath 122. Compression of the wire can also cause flexure of the sheath in the opposite direction. In one variation, the sheath 122 can be attached to the housing 104 of the cutting assembly 102. Since the housing 104 is rotatable relative to the cutter 108 and the torque shaft 114, the sheath 122 can rotate independently of the torque shaft 114 and cutter 108 to either sweep the cutting assembly 102 or to change direction of the articulated cutting assembly 102 at an independent rate.

Figure 12B:
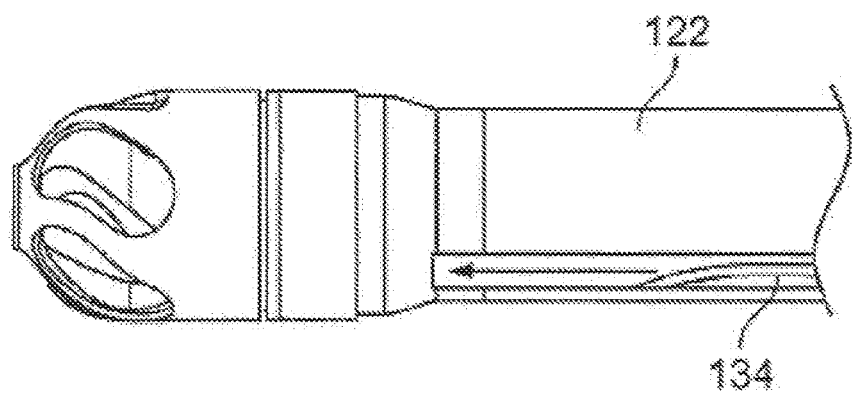
Figure 12C:
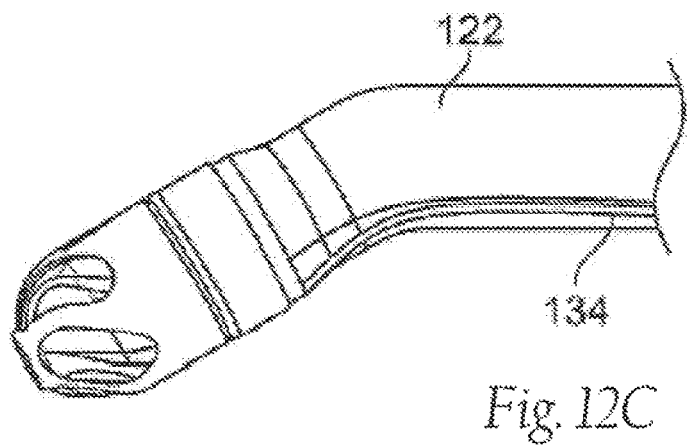

In another variation of the device 100, as shown in FIG. 12B, a preshaped curved wire or mandrel 134 can be advanced in a lumen in either the sheath 122 or catheter 120. As the mandrel 134 advances, the device takes the shape as shown in FIG. 12C.

In yet another variation, the catheter tip and cutting assembly can be articulated in different directions and swept through an arc by having a series of sliding pull wires running through side lumens in the sheath. The pull wires attach to the cutter assembly. By cycling tension on the pull wires sequentially on the proximal control with such mechanism as a cam, the deflected tip can be swept in an arc.

Figure 12D:
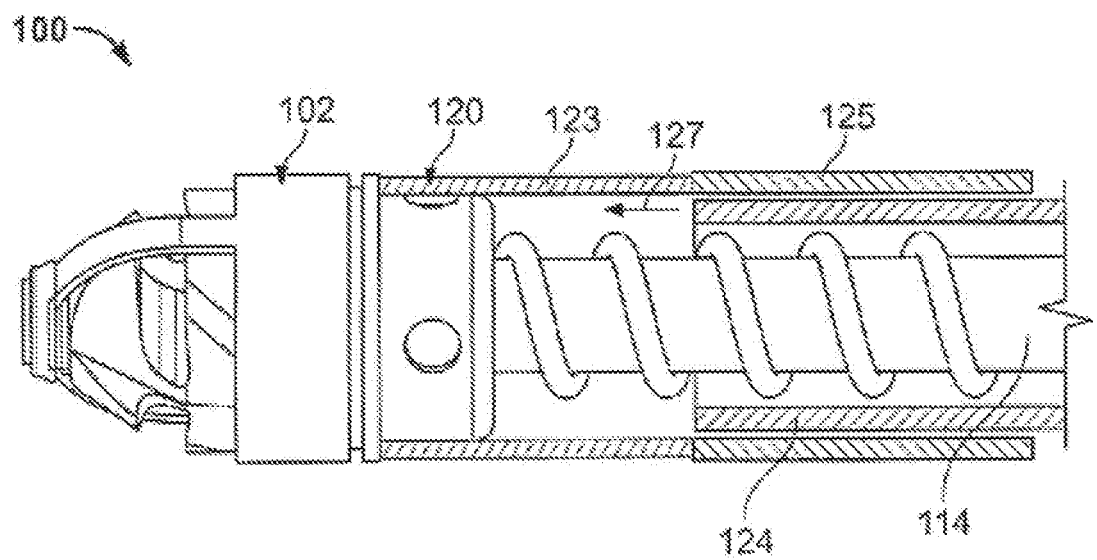
Figure 12E:
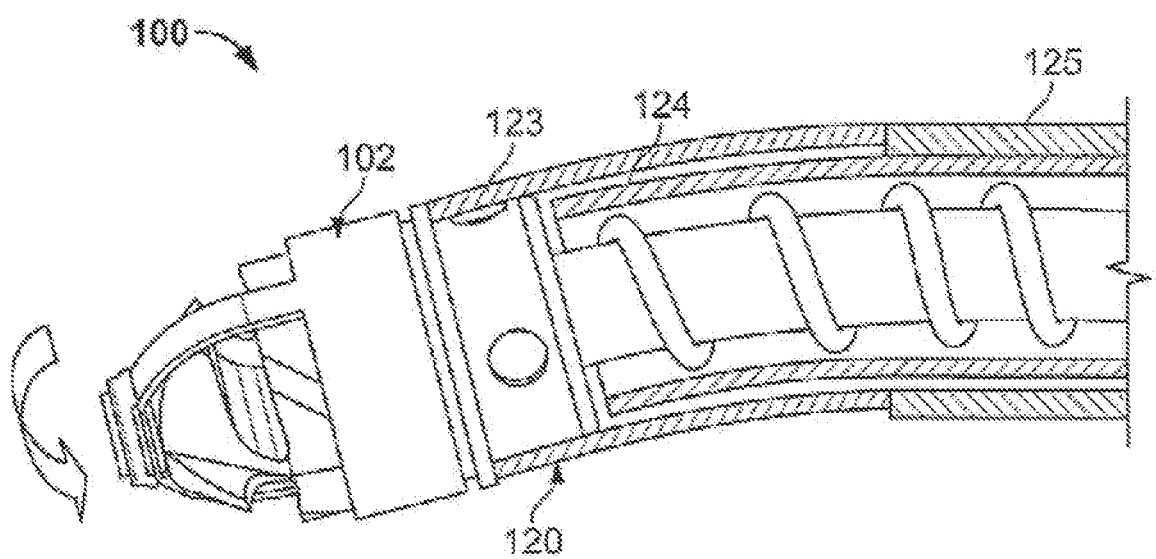

FIGS. 12D to 12E illustrate a variation of a device 100 having a pre-shaped sweep sheath for a deflecting member 124 located in a space between the catheter 120 and the torque shaft 114. In this variation, the catheter 120 includes a flexible distal portion 123 and a relatively stiffer proximal portion 125. When the sweep sheath 124 is located within the stiffer proximal portion 125 of the catheter lumen the sweep sheath 124 straightens. To articulate the cutter assembly 102, the operator advances the sweep sheath 124 as shown by arrow 127 such that the sweep sheath 124 locates within the flexible distal portion 123 of the catheter 120. As a result, and as shown in FIG. 12B, the sweep sheath 124 causes articulation of the cutter assembly 102. The sweep sheath 124 is rotatable as well as axially moveable within the catheter 124. As a result, rotation of the sweep sheath 124 sweeps the cutter assembly 102 in an arc as discussed above.

As shown, the catheter body 120 remains stationary while the inner sweep sheath 124 rotates to move the cutting assembly 102 in an arc or orbit within the lumen. The outer catheter 120 body provides a static linkage between the cutter assembly and the deflection control assembly. The outer sheath is preferably composed of a metal braid sandwiched in a polymeric matrix of such materials as high density polyurethane (HDPE), polyethylene (PE), fluoropolymer (PTFE), nylon, polyether-block amide (PEBAX), polyurethane, and/or silicone. The sheath is stiffer proximally than distally. This can be achieved by using softer grades of polymers distally and/or having no metal braid distally.

FIGS. 13A and 13B illustrate one variation of a control system or fixture. As shown, the control system 200 includes a sweep control knob 202 coupled to a sweep sheath (not illustrated.) The sweep control knob 202 can slide axially and rotate independently relative to the outer catheter 120 and the torque shaft (not shown). Again, the sweep sheath can be composed of a metal braid sandwiched in a polymeric matrix of such materials as polyethylene (PE), fluoropolymer (PTFE), nylon, and/or polyether-block amide (PEBAX), polyurethane, and/or silicone. The sweep sheath can also be made of counter wound metal coils. Its distal end is curved and is preferably made of a material that can withstand high degree of flex and retain its curved shape. Such material may include polymers such as PE, nylon, Polyetheretherketone (PEEK), Nickel Titanium (Nitinol), or spring steel.

To allow the cutter assembly to be straight and undeflected 102, the sweep sheath is withdrawn proximally by the sweep control knob 202. This causes the curved or shaped section of the sweep sheath to retract within the stiff portion of the outer catheter 120. As shown in FIG. 13A, distal movement of the sweep control knob 202 advances the sweep sheath to deflect the catheter tip. The degree of the deflection is controlled by the amount the sweep sheath is advanced. The more the curve of the sweep sheath protrudes distal to the stiff section of the outer sheath, the more the catheter deflects.

As shown in FIG. 13B, the sweep control knob 202 can be rotated to sweep the cutting assembly 102 in an arc manner. Although sweeping of the cutting assembly 102 can occur via manual operation. Variations of the device include sweep sheaths that can be selectively coupled to a motor to activate an automated rotation. This allows the physician to have a smooth, continuous, automated means to sweep the cutter without any manual effort.

Figure 13C:
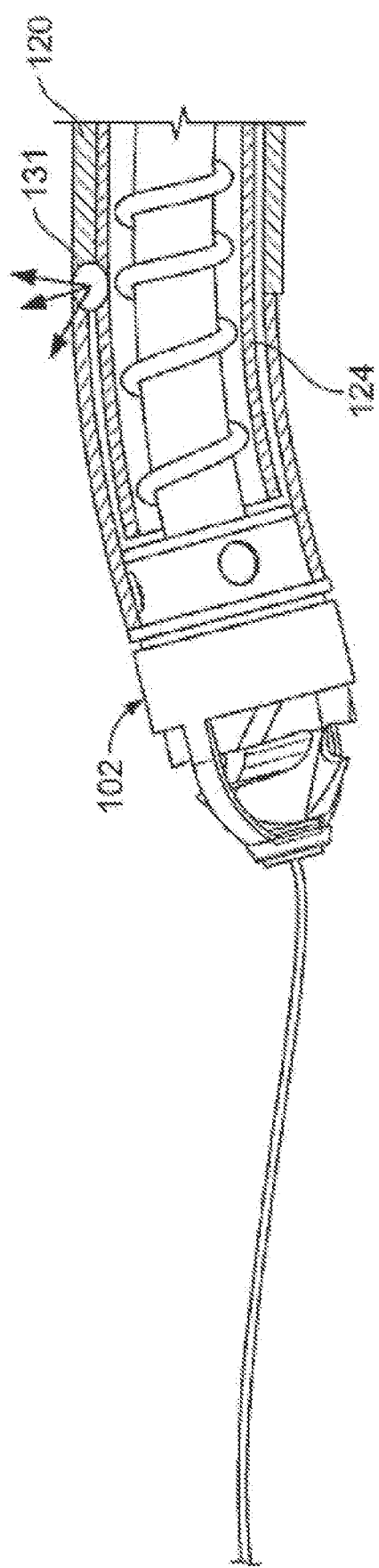
FIG. 13C shows a perfusion port at a distal portion of the device.

FIGS. 13A and 13B also show the catheter 120 as having a flush port 129. The flush port 129 provides a means for injecting a fluid such as heparinized saline or any other medicine into the catheter body 120 to keep blood and tissue debris from clogging the space between components in the device. The flush port 129 can also help lubricate moving components within the device. One desirable fluid path is along the length of the catheter in the space between the catheter body 120 and sweep sheath 124. Drugs or fluids can be introduced via the flush port 129 for flow out of one or more openings 131 near the catheter tip or cutting assembly 102. In some variations, it may be desirable to place a flush opening 131 at an "elbow" of the catheter body 120 as shown in FIG. 13C. During use of the catheter the tip is deflected, the "elbow" always contacts the luminal surface. Drugs flushing out this elbow can then infuse into the vessel wall. Using a stenosis-inhibiting drug like paclitaxel or rapamycin could help prevent restenosis after the atherectomy procedure.

Figure 13D:
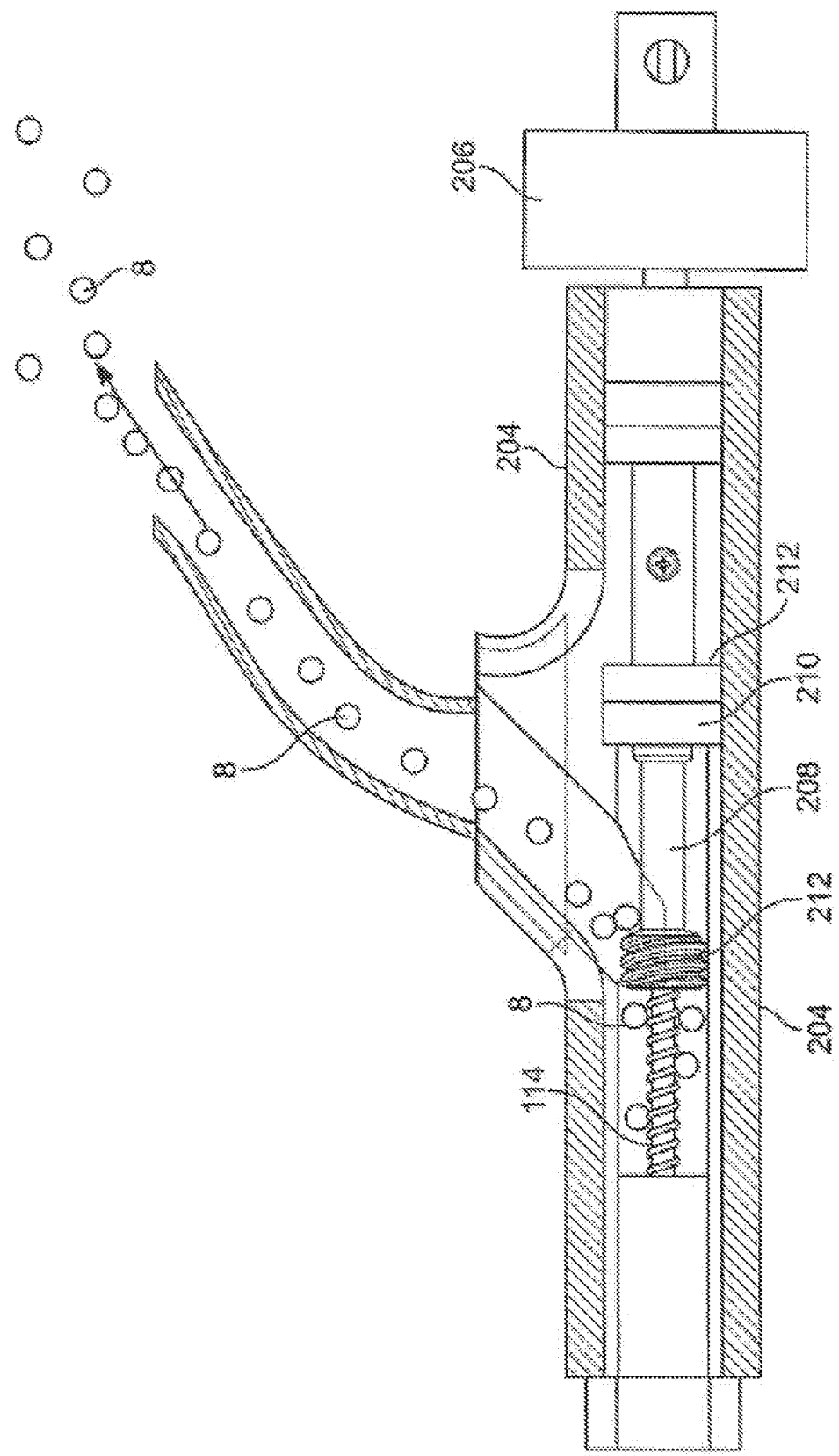
FIG. 13D shows a cross sectional view of a portion of the catheter hub mechanism that removes debris from the device.
Figure 14A:
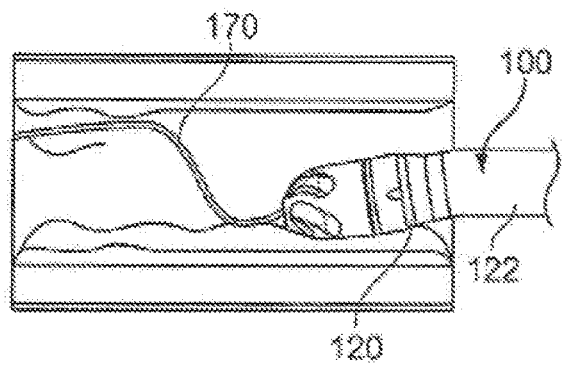
FIGS. 14A-14F show additional variations of the device for articulating the cutting assembly.
Figure 14B:
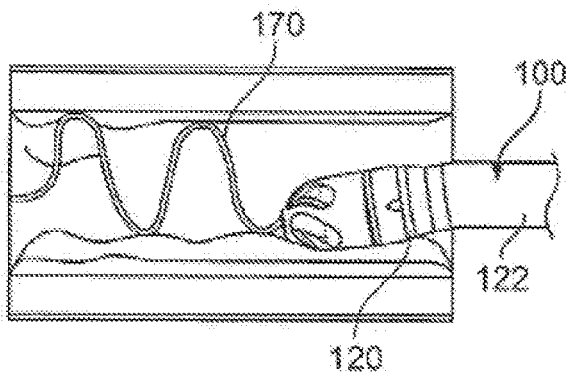
Figure 14C:
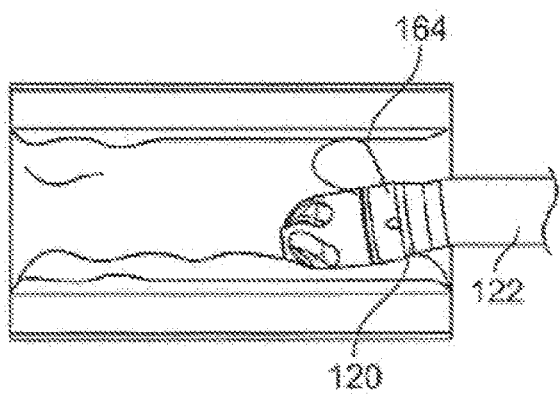
Figure 14D:
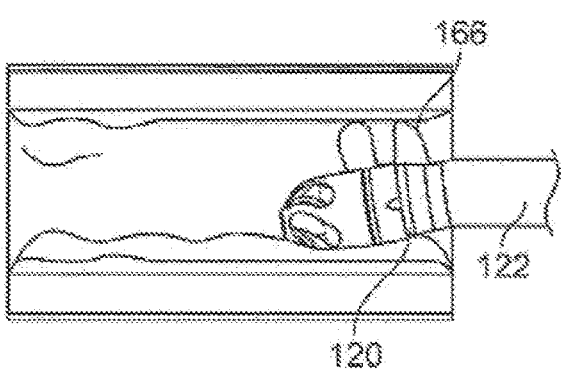
Figure 14E:
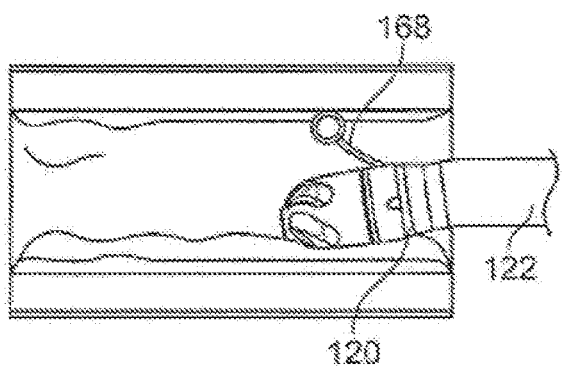
Figure 14F:
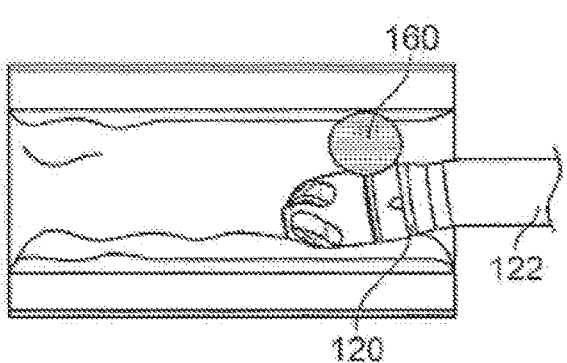

Turning now to a variation of the catheter 100 and control system 200, the entire system is arranged from distal to proximal with a cutter assembly 102, a catheter body 120, a flush port 129, a control system 200 for tip deflection and sweep control, a hub 204 or other connection for providing aspiration of the cut materials as well as a drive gear 206 to turn the torque shaft and cutter. The gear 206 is connected to a rigid drive shaft 208 encased within the hub 204 as shown in FIG. 13D. The drive shaft 208 can take a form of a hollow tube with a central lumen for passage of the guidewire and is centered within a lumen in the hub 204 and fixed axially by a pair of bearings 210. A seal 212 adjacent to the bearing 210 prevents aspirated tissue debris from leaking proximally through the bearing 210. A transfer propeller 212 is rigidly attached to the distal portion of the drive shaft 208 to pump aspirated tissue debris 8 from the catheter out into an attached aspiration reservoir. The drive shaft 208 is connected to flexible torque shaft 114 that extends the length of the catheter body for the purpose of transfer torque from the drive shaft to the cutter. As noted above, the torque shaft 114 has helical grooves on its outer diameter and central guidewire lumen. During a procedure run, a motor drives the gear 206 to rotate. This causes rotation of the drive shaft 208, the transfer propeller 212, the torque shaft 114, and the cutter (not shown) all in the same rotational sense. Thus the cutter assembly effectively cuts plaque and drives the debris back into the helical groove on the torque shaft 114. The rotating helical grooves winds the debris back into the hub 204, which is then transferred to the aspiration reservoir by the transfer propeller 212. The propeller 212 can take the form of a screw or a series of circumferentially arranged angled fan blades. The cutter is preferably rotated at a speed of 10,000-25,000 rpm. An alternative design would have the aspiration reservoir built into the hub of the catheter.

FIGS. 14A to 14F illustrate additional mechanisms for flexing the device 100. Such mechanisms can include side balloons 160, meshes, wire loops 164, coils 166, and arms or mandrels 168 and other such structures. These features can be incorporated into catheter body 120 itself or into the sheath 122. If located in the catheter body 122, the entire catheter can be rotated to steer the tip in different directions. A curved or helical guidewire 170 can also be used to effect the flexion of the catheter tip as shown in rigs. 14A to 14F. The wire can also be actively flexed to control the degree of catheter flexion. All of these deflecting mechanisms can cause the catheter to be deflected in one plane or it can be deflected in three dimensions. The curve on the wire can be in one plane or in 3 dimensions. The sheath can be flexed in one plane or 3 dimensions. Another way to achieve flexion at the distal tip of the catheter is to only partially jacket the distal end with one or more polymers. A bevel at the distal end and/or varying combinations of jacketing and polymers can be used to change the position of the moment arm. This changes the flexibility of the distal end and allows proper deflection.

In addition to providing a means for deflecting the catheter, and allowing the user to sweep the distal tip to engage the lesion as desired, it is also possible to link a separate torque control device to manually or automatically control the sweep of the catheter, independent of the axial control of the catheter insertion and the rotation control of the cutter within the housing. Automatic control may be performed open-loop by user entered settings and activating a switch, or with feedback control designed to further optimize cutting effectiveness, procedural efficiency, and safety. Example structures of how to lock the articulation of the sheath/catheter into place include a lockable collar, a stopper, and friction lock detect mechanisms with one or more springs, coils, or hinges.

Additional components may be incorporated into the devices described herein. For example, it can be desirable to incorporate transducers into the distal region of the catheter to characterize the plaque or to assess plaque and wall thickness and vessel diameter for treatment planning; also transducers may be desired to indicate the progression of debulking or proximity of cutter to vessel wall. For example, pressure sensors mounted on the catheter housing can sense the increase in contact force encountered in the event that the housing is pressed against the vessel wall. Temperature sensors can be used to detect vulnerable plaque. Ultrasound transducers can be used to image luminal area, plaque thickness or volume, and wall thickness. Optical coherence tomography can be used to make plaque and wall thickness measurements. Electrodes can be used for sensing the impedance of contacted tissue, which allows discrimination between types of plaque and also vessel wall. Electrodes can also be used to deliver impulses of energy, for example to assess innervation, to either stimulate or Inactivate smooth muscle, or to characterize the plaque (composition, thickness, etc.). For example, transient spasm may be introduced to bring the vessel to a smaller diameter easier to debulk, then reversed either electrically or pharmaceutically. Electrical energy may also be delivered to improve the delivery of drugs or biologic agents, by causing the cell membrane to open in response to the electric stimulation (electroporation). One method of characterization by electrical measurement is electrical impedance tomography.

Figure 15:
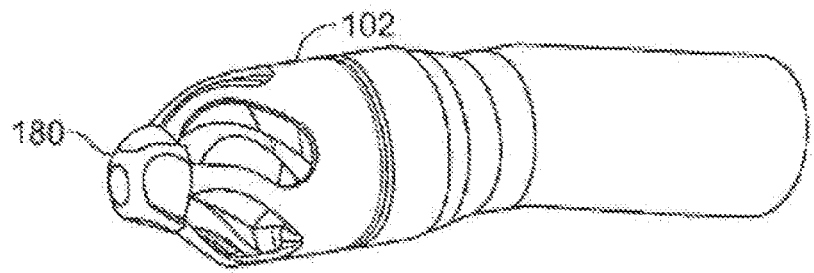
FIG. 15 shows a device with a burr tip.

As shown in FIG. 15, a cutter assembly 102 can also have a burr protruding out its nose. Although the burr 180 may have any type of abrasive surface, in one variation, this burr is blunt and has fine grit (such as diamond grit) to allow for grinding of heavily calcified tissue without injuring adjacent soft tissue. This combination of a burr and cutter allow the distal assembly to remove hard stenotic tissue (calcified plaque) using the burr while the sharp-edged shaving cutter removes softer tissue such as fibrous, fatty tissue, smooth muscle proliferation, or thrombus. In variations, the burr can also have helical flutes to help with aspiration, or the burr can be incorporated to a portion of the cutting edge (for example, the most distal aspect of the cutter).

Figure 16A:
FIGS. 16A-16C provide examples of fluid delivery systems.
Figure 16B:
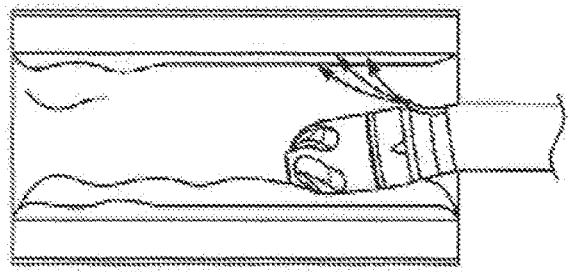
Figure 16C:
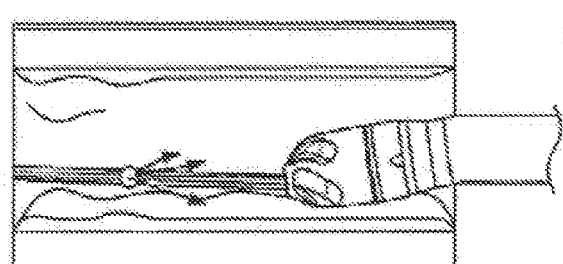

Infusing solutions (flush) into the target treatment site may be desireable. Infused cool saline can prevent heating of blood and other tissue, which reduces the possibility of thrombus or other tissue damage. Heparinized saline can also prevent thrombus and thin out the blood to help maximize effectiveness of aspiration. The flush can also include drugs such as Clopidegrel, Rapamycin, Paclitaxel or other restenosis-inhibitors. This may help to prevent restenosis and may result in better long term patency. The flush may include paralytics or long-acting smooth muscle relaxants to prevent acute recoil of the vessel. FIGS. 16A-16C illustrate variations of flushing out the device 100. The flush can be infused through the guide wire lumen (FIG. 16A), a side lumen in the catheter shaft (FIG. 16B) or tube, the space between the flexing sheath and the catheter and/or the sideports in the guidewire (FIG. 16C). Flush can come out of a port at the distal end of the cutter pointing the flush proximally to facility aspiration. Alternatively, by instilling the flush out the distal end of the cutter housing over the rounded surface, the flow may be directed rearward by the Coanda effect. The restenosis-inhibitors can be carried by microcapsules with tissue adhesives or velcro-like features on the surface to stick to inner vessel surface so that the drug adheres to the treatment site, and to provide a time-release controlled by the resorption or dissolving of the coating to further improve efficacy. Such velcro-like features may be constructed with nanoscale structures made of organic or inorganic materials. Reducing the volume of foreign matter and exposing remaining tissue and extracellular matrix to drugs, stimulation, or sensors can make any of these techniques more effective.

Another way to infuse fluid is to supply pressurized fluid at the proximal portion of the guidewire lumen (gravity or pressure feed) intravenous bag, for example. A hemostatic seal with a side branch is useful for this purpose; tuohy-borst adapters are one example of a means to implement this.

Balancing the relative amount of infusion versus fluid volume aspirated allows control over the vessel diameter; aspirating more fluid than is instilled will evacuate the vessel, shrinking its diameter, and allow cutting of lesion at a greater diameter than the atherectomy catheter. This has been a problem for certain open cutter designs that use aspiration, because the aggressive aspiration required to trap the embolic particles evacuates and collapses the artery around the cutter blades; this is both a performance issue because the cutter can bog down from too high torque load, and the cutter can easily perforate the vessel. The shielded design described here obviates both problems, and further requires less aggressive aspiration to be effective, giving a wider range of control to the user.

Figure 17:
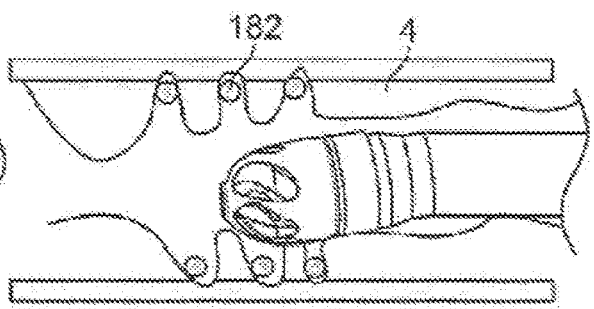
FIG. 17 shows the device placed within a stent or coil.

The devices of the present invention may also be used in conjunction with other structures placed in the body lumens. For example, as shown in FIG. 17, one way to protect the vessel and also allow for maximum plaque volume reduction is to deploy a protective structure such as a stent, thin expandable coil or an expandable mesh 182 within a lesion. As this structure expands after deployment, the thin wire coil or the struts push radially outward through the plaque until it becomes substantially flush with the vessel wall. This expansion of thin members requires minimal displacement of plaque volume and minimizes barotrauma produced in balloon angioplasty or balloon expanded stent delivery. Once the protective structure has expanded fully, atherectomy can be performed to cut away the plaque inside to open up the lumen. The vessel wall is protected by the expanded structure because the structure members (coil or struts) resist cutting by the atherectomy cutter, and are disposed in a way that they cannot invaginate into the cutter housing (and thereby be grabbed by the cutter). It is also possible to adjust the angle of the windows on the atherectomy catheter cutter housing so that they do not align with the struts or coils; the adjustment to orientation may be accounted for in the coil or strut design, in the cutter housing design, or both. Furthermore, the protective member can be relatively flexible and have a low profile (thin elements), so that it may be left in place as a stent. Because the stent in this case relies mainly upon atherectomy to restore lumen patency, it may be designed to exert far less radial force as it is deployed. This allows usage of greater range of materials, some of which may not have as high of stiffness and strength such as bioresorbable polymers and metal alloys. Also, this allows a more resilient design, amenable to the mechanical forces in the peripheral arteries. It also minimizes flow disruption, to minimize hemodynamic complications such as thrombosis related to the relatively low flows found in the periphery. It is also possible to perform atherectomy prior to placing the protective structure, whether or not atherectomy is performed after placing the structure.

Figure 18A:
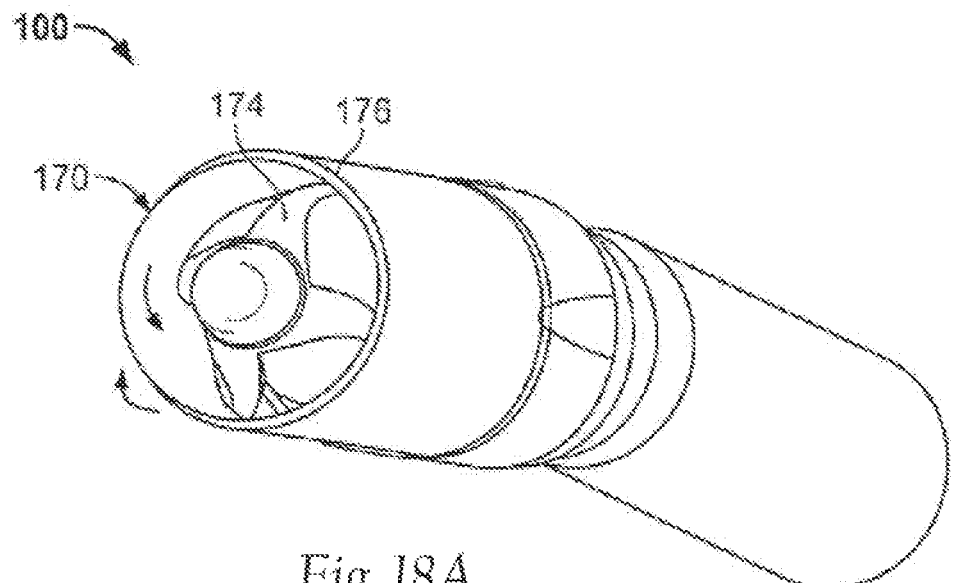
FIGS. 18A-18B show variations of devices for removing tissue from body lumens.
Figure 18B:
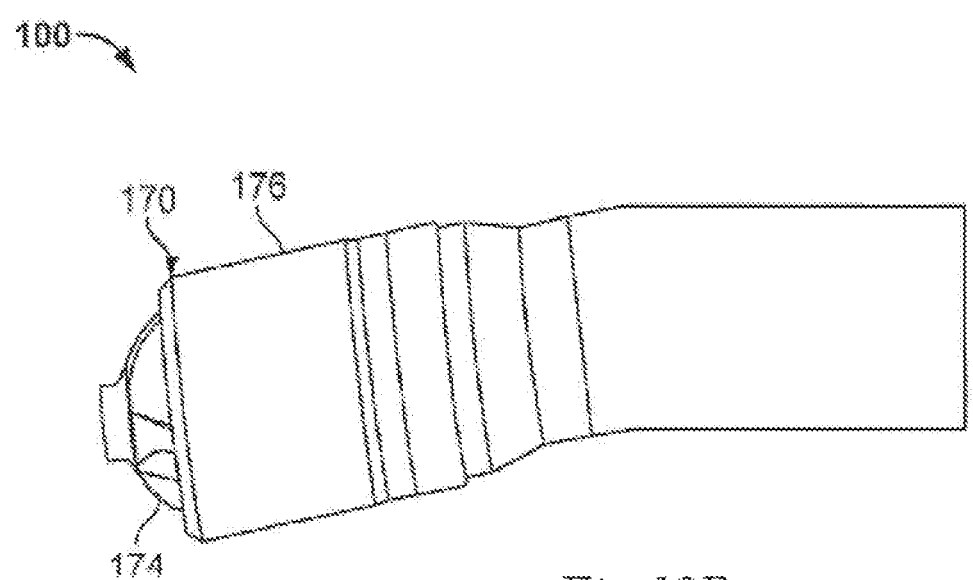
Figure 19A:
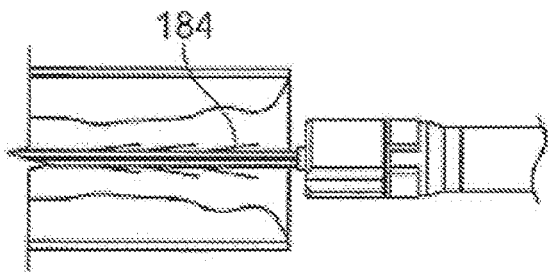
FIGS. 19A-19F show additional variations for centering devices within a lumen.
Figure 19B:
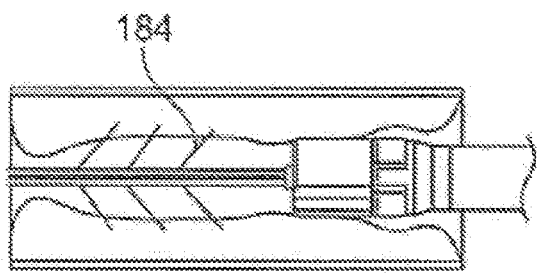
Figure 19C:
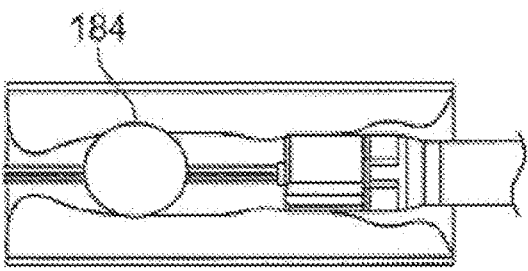
Figure 19D:
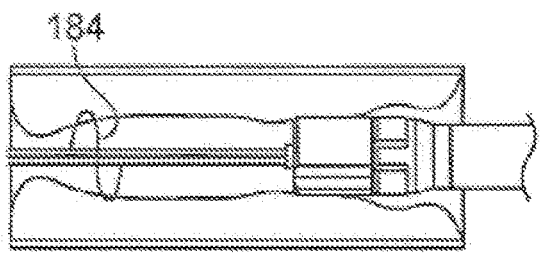
Figure 19E:
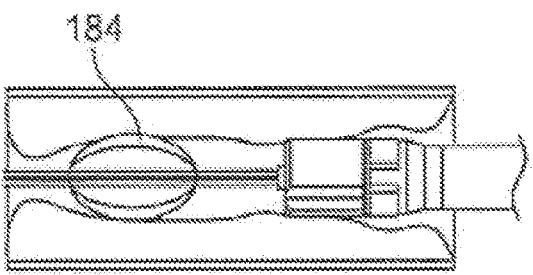
Figure 19F:
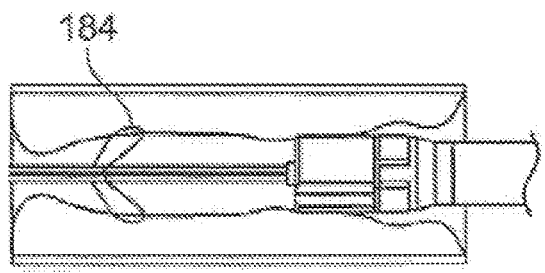
Figure 19G:
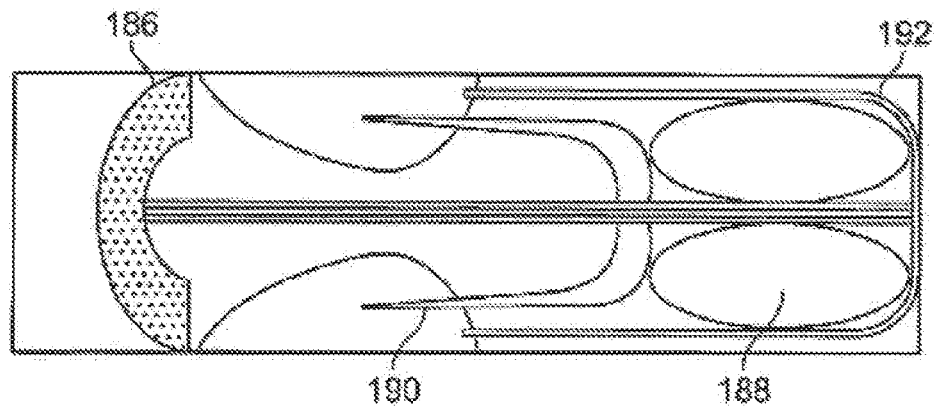
FIG. 19G shows a balloon actuated device for treating occlusions.

Additional variations of systems include devices 100 having a cutting assembly 170 comprising spinning turbine-like coring cutter 172 as shown above and as shown in FIG. 18A. FIG. 18B shows a side view of the coring cutter 170. In use, the coring cutter can be hydraulically pushed to drive the sharp edge through tissue. The turbine like cutters has helical blades 174 on the inside of the sharp cylinder housing 176 (shell). The coring cutter 170 may also have spokes or centering devices 184 as shown to in FIGS. 19A to 19F center the shell about the guidewire. This helps to keep the cut of the plaque centered about the vessel wall for safety. The spokes also act as an impeller to pull stenotic tissue back and this helps to drive the cutter forward as well as achieve aspiration to minimize embolization. In the hydraulically driven cutter design, an anchor 186 is deployed in tissue and is connected to a backstop 192. A balloon or hydraulic chamber 188 is then pressurized to expand and pushes the cutting blade 190 forward through the lesion (See FIG. 19G). One advantage of this approach may be that the technique is similar to angioplasty (which involves pumping up a balloon with an endoflator). One means of anchoring is to use an anchoring guidewire, for example, a guidewire with an inflatable balloon to be placed distal to the atherectomy catheter. Alternatively, the technique of anchoring distally can be used with the previously described torque shaft driven atherectomy catheter.

It is also possible to use the devices and methods described here to restore patency to arterial lesions in the coronary circulation and in the cerebrovalscular circulation, both by debulking de novo lesions and by debulking in stent restenosis.

The devices and methods described herein also work particularly well in lesions that are challenging to treat with other methods: at bifurcations, in tortuous arteries, and in arteries which are subject to biomechanical stresses (such as in the knee or other joints).

In a further variation of the devices described here, the motor drive unit may be powered by a controller that varies the speed and torque supplied to the catheter to optimize cutting efficiency or to automatically orbit the cutter using variable speed with a fixed flexible distal length of catheter (or providing further orbiting control by controlling the length of the distal flexible section of the catheter).

It is also possible to use feedback control to operate the catheter in a vessel safe mode, so that the rate of cutting is decreased as the vessel wall is approached. This may be accomplished through speed control, or by reducing the degree to which the cutting blades penetrate above the housing window by retracting the cutter axially within the housing. Feedback variables could be by optical (infrared) or ultrasound transducer, or by other transducers (pressure, electrical impedance, etc.), or by monitoring motor performance. Feedback variables may also be used in safety algorithms to stop the cutter, for example in a torque overload situation.

The atherectomy catheter may be further configured with a balloon proximal to the cutter, for adjunctive angioplasty or stent delivery. The catheter may optionally be configured to deliver self-expanding stents. This provides convenience to the user and greater assurance of adjunctive therapy at the intended location where atherectomy was performed.

Further methods include use of similar devices to debulk stenosis in AV hemodialysis access sites (fistulae and synthetic grafts), as well as to remove thrombus. By removing the cutter housing and recessing the fluted cutter within the catheter sheath, a suitable non-cutting thrombectomy catheter may be constructed.

Other methods of use include excising bone, cartilage, connective tissue, or muscle during minimally invasive surgical procedures. For example, a catheter that includes cutting and burr elements may be used to gain access to the spine for performing laminectomy or facetectomy procedures to alleviate spinal stenosis. For this application, the catheter may be further designed to deploy through a rigid cannula over part of its length, or have a rigid portion itself, to aid in surgical insertion and navigation.

For this reason, it is advantageous to couple atherectomy with stenting. By removing material, debulking the lesion, a lesser radial force is required to further open the artery and maintain lumen diameter. The amount of debulking can be tuned to perform well in concert with the mechanical characteristics of the selected stent. For stents that supply greater expansion and radial force, relatively less atherectomy is required for satisfactory result. An alternative treatment approach is to debulk the lesion substantially, which will allow placement of a stent optimized for the mechanical conditions inherent in the peripheral anatomy. In essence, the stent can support itself against the vessel wall and supply mild radial force to preserve luminal patency. The stent may be bioresorbable, and/or drug eluting, with the resorption or elution happening over a period for days to up to 12 weeks or more. A period of 4 to 12 weeks matches well with the time course of remodeling and return to stability as seen in the classic wound healing response, and in particular the known remodeling time course of arteries following stent procedures. In addition, the stent geometry can be optimized to minimize thrombosis by inducing swirl in the blood flow. This has the effect of minimizing or eliminating stagnant or recirculating flow that leads to thrombus formation. Spiral construction of at least the proximal (upstream) portion of the stent will achieve this. It is also beneficial to ensure that flow immediately distal to the stent does not create any stagnant or recirculation zones, and swirl is a way to prevent this also.

Figure 20A:
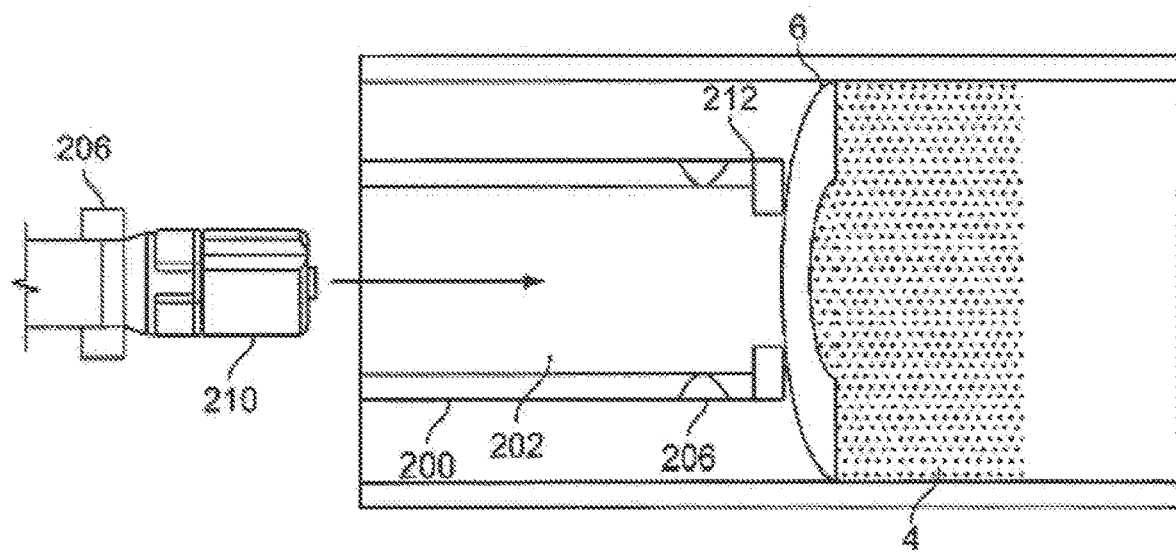
FIGS. 20A-20C show a system for visualizing and crossing total occlusions.

FIG. 20A illustrates another variation of a device for clearing obstructions within body lumens. In some cases where a vessel is totally occluded, a tough fibrous or calcific cap 6 completely or almost completely blocks the lumen. Because of this blockage, fluid cannot flow past the occlusion. This stagnation also makes it difficult or impossible to properly insert a wire across the lesion with an atherectomy device or stiff catheter.

In a typical case of a total occlusion, it is also difficult if not impossible to visualize the lumen near the occlusion because any injected contrast agents cannot flow through the occlusion site.

FIG. 20A shows a system for treating total occlusions. The system can include a support catheter comprising a support tube or catheter 200, having a central lumen 202, the catheter may include side lumens or ports 206, for flush and aspiration. The catheter central lumen 202 can be used to deliver contrast agents 208. In addition, tip centering mechanisms, and an atraumatic tip can be useful. The support catheter can be used with any lumen-creating device 210, such as the devices 100 described above, a laser catheter, an RF probe, or an RF guidewire. When using a coring cutter as shown in FIG. 20A, the cutter can have a sharp edge at its tip, helical flutes, helical grooves, or any other mechanism that enables penetration of the fibrous or calcific cap. The cutter and the shaft can be advanced forward within the support catheter, and one or more balloons or baskets can also be deployed by the support catheter to help center it in the vessel.

The lumen-creating device 200 can optionally be made to have a shoulder 212 at its distal end, as shown in FIG. 20A. The shoulder 212 acts as a stop to limit the depth at which the device 200 protrudes beyond the support catheter 200. Such a safety measure may be desired to protect the vessel wall. Driving the device 200 through the tough fibrous cap creates a lumen in the cap. A guidewire may then be placed into the lumen created in the fibrous cap. The coring cutter may be removed with the core.

Next, a guidewire can be used with a cutter assembly to remove some or all of the remaining mass in the vessel. Alternatively, the initial lumen made may be adequately large without further atherectomy. Technical success is typically less than 30 percent or less than 20 percent residual stenosis. Also, balloon angioplasty with or without stenting may be per formed following establishment of a guidewire lumen with a support catheter and a lumen-creating catheter.

Figure 20B:
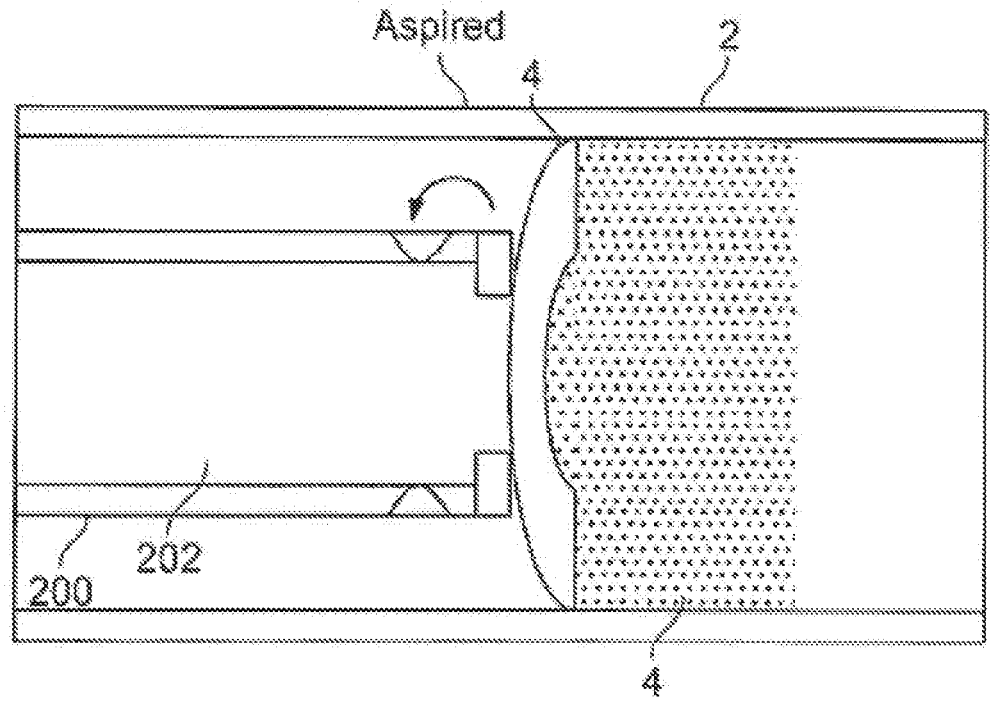
Figure 20C:
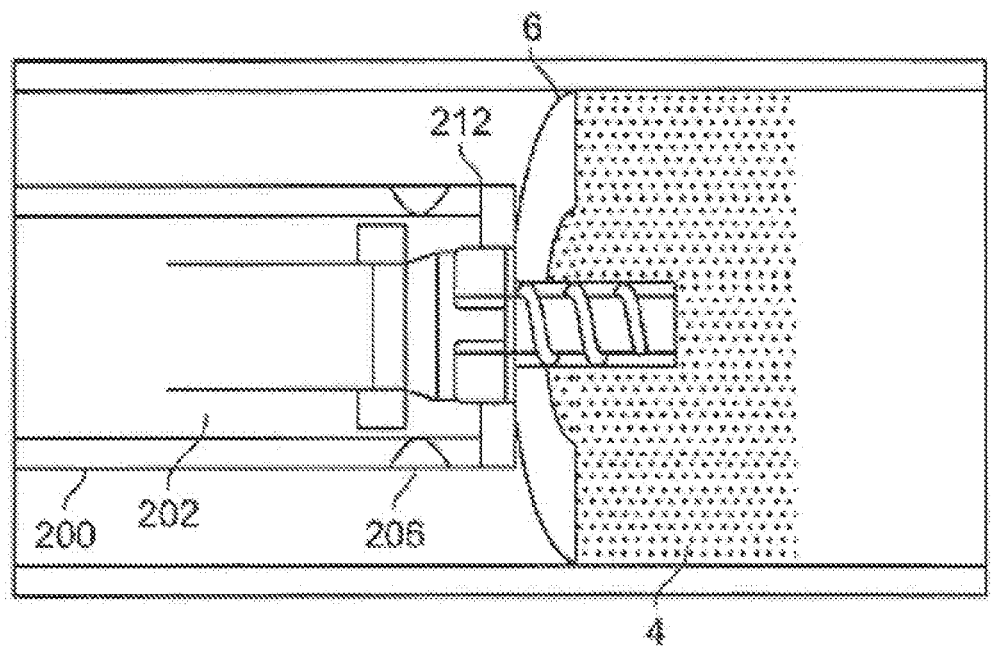

Contrast injection and aspiration ports near the distal end of the support circulate contrast agents, enabling the use of fluoroscopy to visualize the lumen adjacent to the total occlusion during diagnosis or treatment. The central lumen 202 of the support catheter 200 can also be used to inject or aspire the contrast agents 208. The contrast agents can circulate through the center lumen 202 in the support catheter 200 and at least one port 206 in various configurations. The fluid can circulate about the distal tip of the catheter, the motion of the fluid being circular as shown in FIG. 20B. For example, the fluid can be injected through the central lumen 202, travel around the distal tip, and then is aspirated back into the support catheter through ports 206 on the side of the surface of the support catheter 200. To illustrate another possible configuration, the fluid can be ejected through the side ports, and then aspired through the central lumen. This recirculation of the contrast agent permits imaging of the vessel at the site of the occlusion.

Figure 21A:
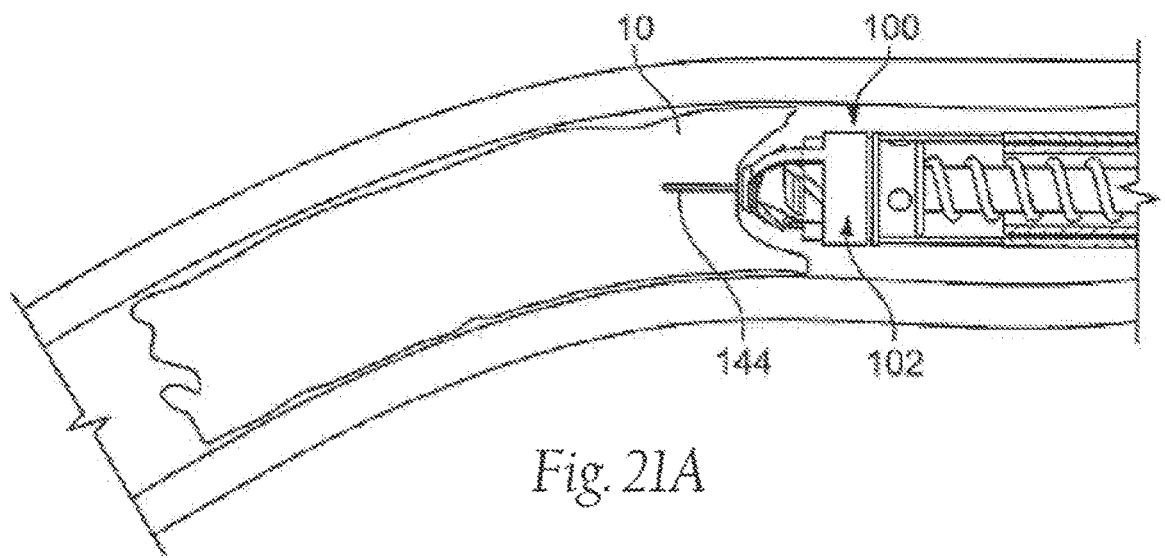
FIGS. 21A-21C shows devices described above for visualizing and crossing total occlusions.

Any of the atherectomy devices 100 described herein can be used as a tool to treat chronic total occlusions (CTO) or a complete blockage of the artery. The frontward cutting and tip-steering capabilities allows the physician to controllably create a channel through the blockage. In one such method for creating this channel (recanalization) the physician places the device 100 proximal edge of a blockage 10 as shown in FIG. 21A.

Figure 21B:
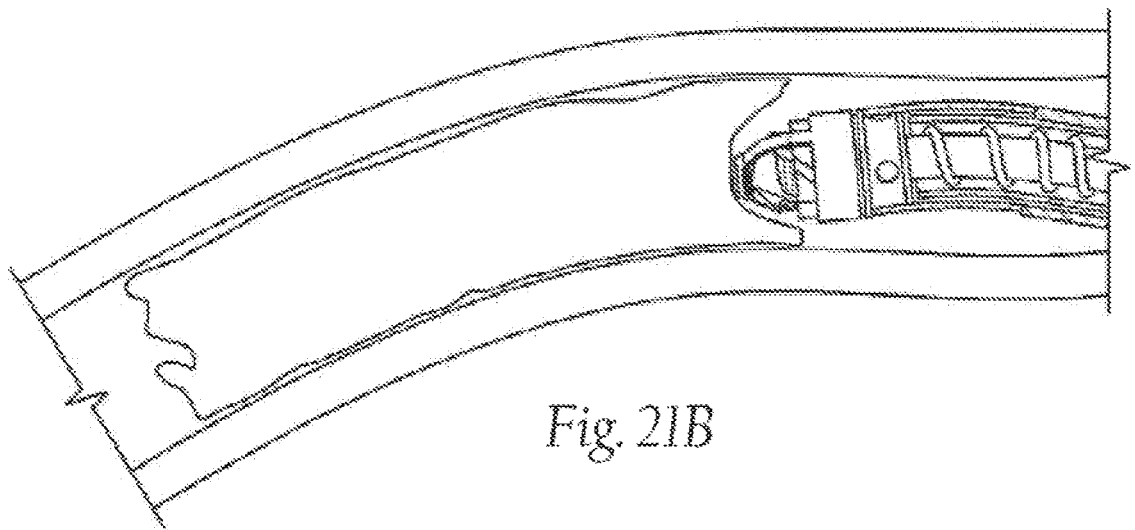
Figure 21C:
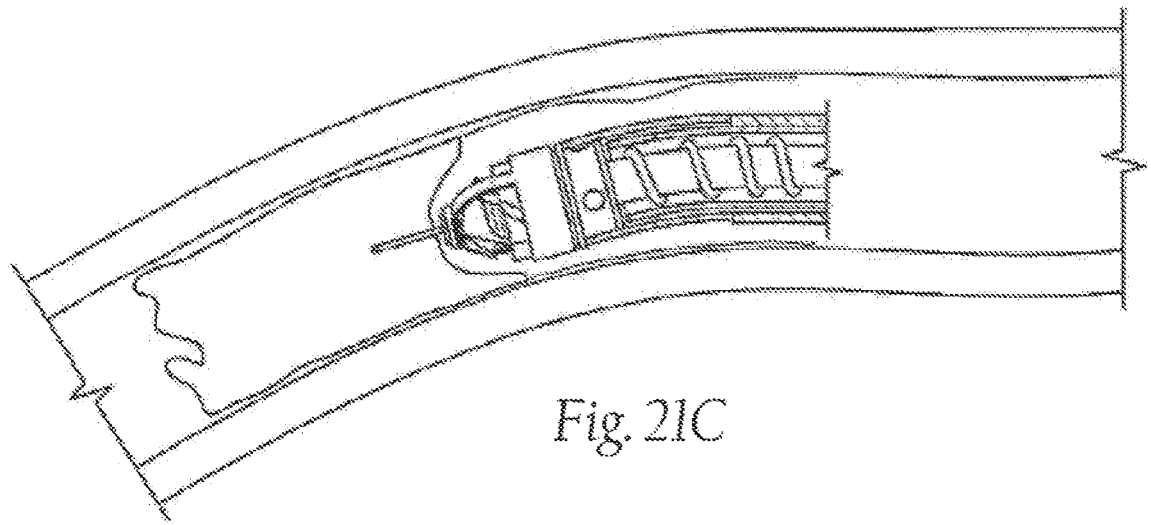

The physician steer the cutting assembly 102 tip towards the center of the vessel as described above. Then, the physician advances a guidewire 144 forward to penetrate the blockage 10. Now that the cutting assembly 102 is located in or adjacent to the blockage 10, the motor is actuated to begin the cutting process allowing the cutting assembly 102 to follow the guidewire 114. During this process, the physician steers the cutting assembly 102 or catheter tip as necessary to keep the cutter centered in the lumen. With the catheter support close to its tip, the wire can be controllably advanced further through the blockage and the catheter can follow by cutting its way forward as shown in FIG. 21C.

The process continues until the cutting assembly 102 passes through the blockage 10. However, during the recanalization process, the guidewire 144 can be exchanged easily, as shown in FIG. 21B, so that the physician can selectively use the optimal guidewire. The catheter has a guidewire lumen that runs along its length and thus allows for this guidewire exchange.

Typically, the physician is not able to visualize the anatomy adjacent to the blockage using the fluoroscope because contrast dye injection cannot be performed due to the complete blockage. The catheter above overcomes this problem because of its ability to aspirate at the cutting assembly. Thus dye injection can be introduced into the target area and circulated back into the catheter via the catheter aspiration mechanism. The flow of dye near the catheter tip allows the physician to visualize the anatomy during the recanalization process.

Figure 22A:
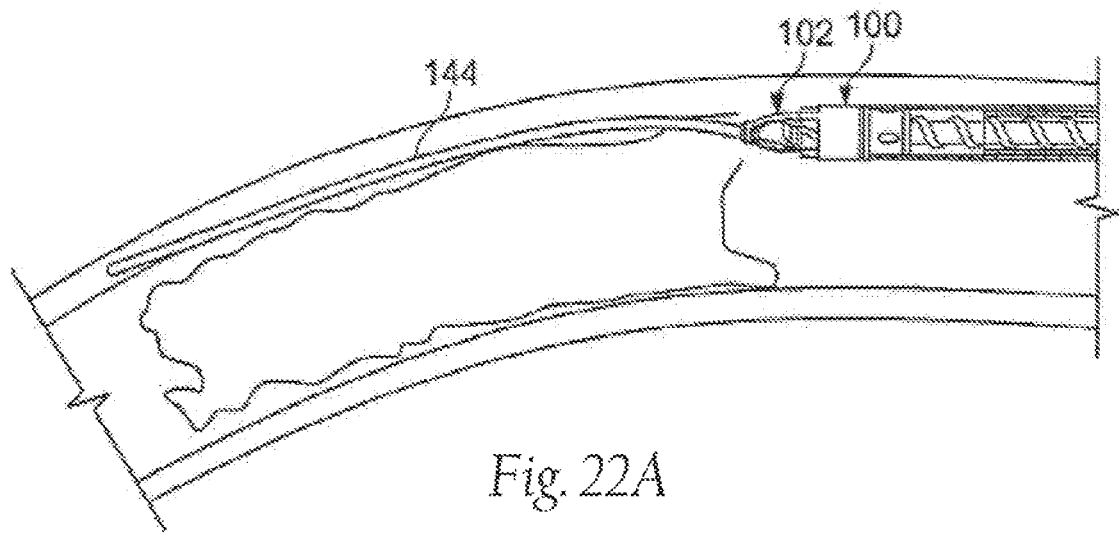
FIGS. 22A-22B shows a variation of crossing a total occlusion by advancing through layers of a vessel.
Figure 22B:
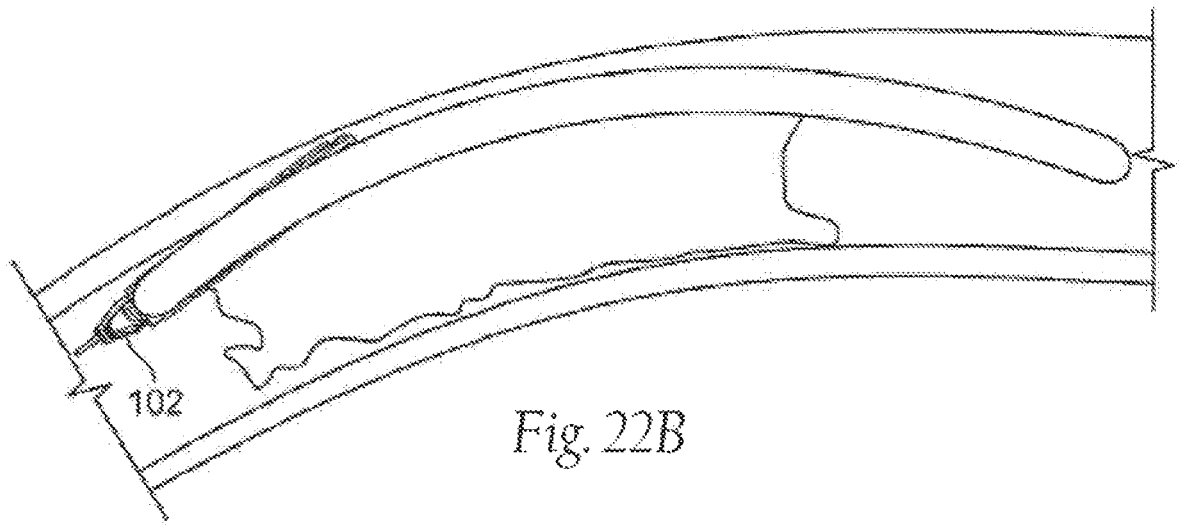

FIGS. 22A and 22B show another method of recanalizing a blockage 10. In this variation, the physician advances the guidewire 144 through the device 100 and between the tissue layers of the vessel (subintimal channel) such as the space between the tunica media (middle layer of vessel wall) and the tunica adventitia (outer elastic layer of the vessel wall). The atherectomy device 100 described herein can be used to provide support for the advancement of the guidewire 144 through the subintimal channel as well as a means for steering back into true lumen. Once the wire has crossed the blockage through the subintimal channel, the device advances forward to follow the guidewire 144 across the blockage 10 and is steered back towards the true lumen as shown in FIG. 228. The cutter assembly 102 can be activated to help pierce a channel into back into the true lumen. In clinical terminology, this catheter is used as a "re-entry device".

The deflected catheter tip is elastic or spring-like. The degree of the deflection is limited by the diameter of the lumen. As plaque is removed during the atherectomy process, the degree of deflection automatically increases. Since the deflected catheter tip is radiopaque (can be visualized with fluoroscope), its degree of deflection can be continuously visualized during the procedure and thus allows the physician to visualize the progress in the opening of the lumen without having to pause and perform a dye injection. Limiting dye injections helps to minimize health problems for the patient and saves procedure time.

Figure 23A:
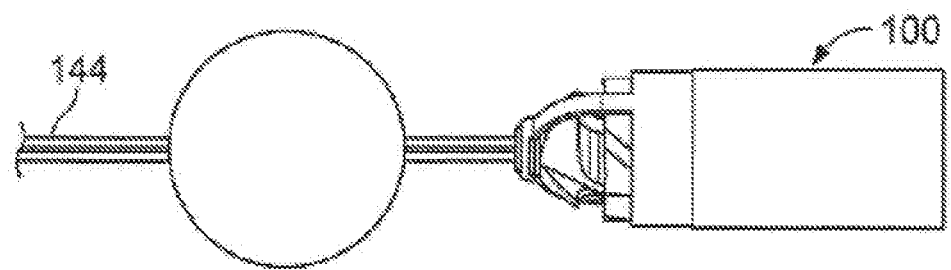
FIGS. 23A-23F show anchoring means on a guidewire for stabilizing devices of the present invention.
Figure 23B:
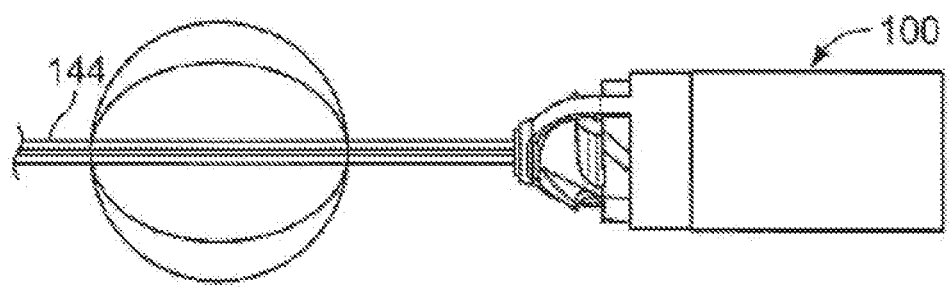
Figure 23C:
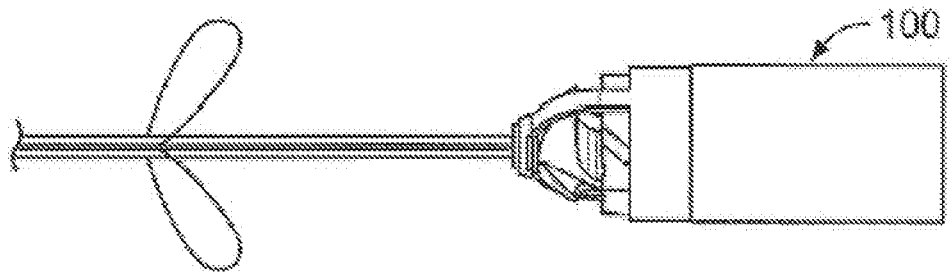
Figure 23D:
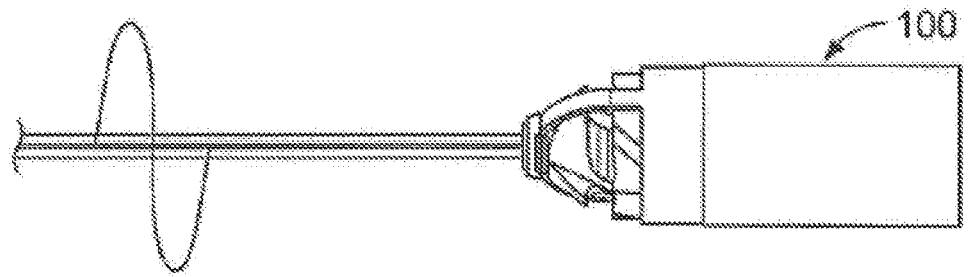
Figure 23E:
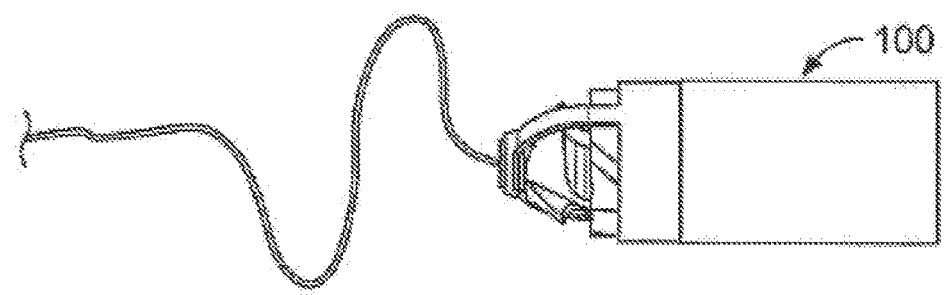
Figure 23F:
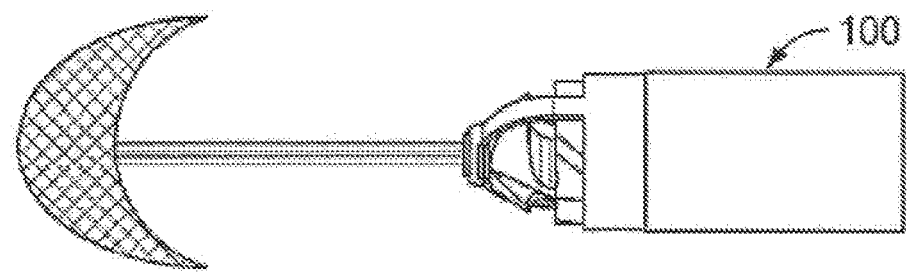

It is important to ensure that the guidewire is axially fixed relative to the target vessel during operation of the atherectomy device 100 to prevent the guidewire tip 144 from traumatizing the vessel. This can be accomplished by having an anchoring mechanism 154 to anchor the wire to the vessel. The mechanism 154 can be an inflatable balloon on the wire as shown in FIG. 23A, expandable basket as shown in FIG. 23B, deployable loops as shown in FIG. 23C, a deployable helical coil FIG. 23D, a wire taking on a shape of a helical coil or a wave on the guidewire FIG. 23E, a porous umbrella or a mesh as shown in FIG. 23F. These mechanisms can all collapse compactly onto profile as small as a typical guidewire to pass through the guidewire lumen on the catheter and expand as large as the distal vessel diameter to anchor. These mechanisms can also act as a way to prevent plaque debris from floating down stream to provide a type of embolic protection.

It is noted that the descriptions above are intended to provide exemplary embodiments of the devices and methods. It is understood that, the invention includes combinations of aspects of embodiments or combinations of the embodiments themselves. Such variations and combinations are within the scope of this disclosure.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A device for removing material from a body lumen, the device comprising:
   a catheter having a proximal end, a distal end, and a catheter lumen extending therethrough;
   a housing coupled to the catheter, the housing comprising a front face having a first opening and a second opening located distal to the first opening and configured to allow passage of a guidewire therethrough;
   a cutter protruding through the first opening, the cutter including a proximal cutter portion comprising a shaft and a distal cutter portion mounted around the shaft of the proximal cutter portion each having a plurality of cutting edges disposed within the housing and protruding distally from the front face of the housing, wherein the proximal cutter portion comprises a number of cutting edges greater than a number of cutting edges of the distal cutter portion, wherein the cutting edges are disposed symmetrically about a longitudinal axis of the cutter and at a same position along the longitudinal axis of the cutter; and
   a torque shaft extending through the catheter lumen and coupled to the cutter for rotating the cutter relative to the catheter.

2. The device of claim 1, wherein the housing is a cylindrical housing attached at the distal end of the catheter.

3. The device of claim 1, further comprising a ferrule comprising a distal bearing surface configured to bear against a proximal surface of the cutter.

4. The device of claim 1, further comprising a drive mechanism at the proximal end of the catheter coupled to the torque shaft for rotating the cutter.

5. The device of claim 1, further comprising a lumen extending through the torque shaft and the cutter accommodating passage of a guide wire.

6. The device of claim 1, wherein the torque shaft has at least one helical conveyor member wound about an exterior such that rotation of the torque shaft conveys material across a length of the torque shaft.

7. The device of claim 1, wherein the plurality of cutting edges are fluted cutting edges.

8. A method for removing material from a body lumen, the method comprising:
   providing an atherectomy device comprising:
   an elongated catheter having a proximal and distal end;
   a housing coupled to the elongated catheter, the housing including a curved surface disposed at a distal end of the housing and a housing opening forming a plane across the curved surface and a second opening; and
   a cutter protruding through the housing opening including a proximal cutter portion comprising a shaft and a distal cutter portion mounted around the shaft of the proximal cutter portion each having a plurality of cutting edges disposed within the housing and protruding from the curved surface of the housing, wherein the proximal cutter portion comprises a number of cutting edges greater than a number of cutting edges of the distal cutter portion, wherein the cutting edges are disposed symmetrically about a longitudinal axis of the cutter and at a same position along the longitudinal axis of the cutter,
   the cutter further including a conical dilator tip connected to a front of the housing and including a dilator opening aligned with the second opening for allowing passage of a guidewire, the conical dilator tip including a tapered surface from the guidewire to the opening to prevent damage to the body lumen;
   positioning the opening adjacent to occlusive material to be removed;
   rotating the cutter such that as the cutting edges rotate through the housing opening the cutting edges protrude above the plane of the housing opening to engage the occlusive material outside of the housing opening; and
   removing the occlusive material.

9. The method of claim 8, wherein the housing is a cylindrical housing attached at the distal end of the elongated catheter.

10. The method of claim 8, wherein the cutter comprises a proximal cutter portion comprising a shaft and a distal cutter portion mounted around the shaft of the proximal cutter portion.

11. The method of claim 10, wherein the atherectomy device further comprises a ferrule comprising a distal bearing surface configured to bear against a proximal surface of the cutter.

12. The method of claim 10, wherein the distal cutter portion comprises at least one helical cutting edge.

13. The method of claim 12, wherein the proximal cutter portion comprises a number of helical cutting edges greater than the at least one helical cutting edge of the distal cutter portion.

14. The method of claim 8, wherein the atherectomy device further comprises a drive mechanism at the proximal end of the catheter coupled to a torque shaft for rotating the cutter.

15. The method of claim 8, wherein the atherectomy device further comprises a lumen extending through a torque shaft and the cutter accommodating passage of a guide wire.

16. The method of claim 8, wherein the torque shaft has at least one helical conveyor member wound about an exterior such that rotation of a torque shaft conveys material across a length of the torque shaft.

17. The method of claim 8, wherein the plurality of cutting edges are fluted cutting edges.

* * * * *